US010299726B2

(12) United States Patent
Tokko et al.

(10) Patent No.: US 10,299,726 B2
(45) Date of Patent: May 28, 2019

(54) BODILY INFORMATION MEASUREMENT APPARATUS

(71) Applicant: OMRON HEALTHCARE Co., Ltd., Kyoto (JP)

(72) Inventors: Yoshihide Tokko, Kyoto (JP); Ryosuke Doi, Kyoto (JP); Yuma Adachi, Kyoto (JP); Chisato Tawara, Kyoto (JP); Minoru Taniguchi, Kyoto (JP); Masayuki Fukutsuka, Kyoto (JP); Eisuke Yamazaki, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 0 days.

(21) Appl. No.: 15/908,720

(22) Filed: Feb. 28, 2018

(65) Prior Publication Data
US 2018/0184925 A1 Jul. 5, 2018

Related U.S. Application Data

(63) Continuation of application No. PCT/JP2016/089054, filed on Dec. 28, 2016.

(30) Foreign Application Priority Data

Jan. 4, 2016 (JP) .................................. 2016-000259
Jun. 9, 2016 (JP) .................................. 2016-115685
Dec. 26, 2016 (JP) .................................. 2016-251967

(51) Int. Cl.
A61B 5/00 (2006.01)
A61B 5/022 (2006.01)
(Continued)

(52) U.S. Cl.
CPC .............. *A61B 5/681* (2013.01); *A61B 5/022* (2013.01); *A61B 5/0205* (2013.01);
(Continued)

(58) Field of Classification Search
None
See application file for complete search history.

(56) References Cited

U.S. PATENT DOCUMENTS 4,896,676 A * 1/1990 Sasaki ................ A61B 5/02241
600/494
5,368,042 A * 11/1994 O'Neal ................ A61B 5/0006
128/905
(Continued)

FOREIGN PATENT DOCUMENTS

JP S63-088860 U 6/1988
JP S63-200144 A 8/1988
(Continued)

OTHER PUBLICATIONS

Definition of "groove", Sep. 26, 2018, Cambridge Dictionary, https://dictionary.cambridge.org/us/dictionary/english/groove.*
(Continued)

*Primary Examiner* — Patricia Mallari
*Assistant Examiner* — Jairo H Portillo
(74) *Attorney, Agent, or Firm* — Osha Liang LLP

(57) ABSTRACT

A bodily information measurement apparatus includes a band-shaped belt to be wrapped around a measurement site; a main body that is connected to a base end portion in the lengthwise direction of the belt and on which a pressure detection unit and a fluid supply unit are mounted; and a fastening unit for fastening the base end portion and the leading end portion of the belt. The belt is formed by stacking an outer circumferential layer and a fluid bladder for compressing the measurement site. The bodily information measurement apparatus is attached to the measurement site due to the base end portion and the leading end portion
(Continued)

being fastened by the fastening portion in a state in which the fluid bladder and the leading end portion of the belt overlap.

6 Claims, 24 Drawing Sheets

(51) Int. Cl.
| | | |
|---|---|---|
| *B29C 65/16* | (2006.01) | |
| *B29C 65/00* | (2006.01) | |
| *B29C 70/84* | (2006.01) | |
| *A61B 5/0205* | (2006.01) | |
| *A61B 5/024* | (2006.01) | |
| *B29L 31/34* | (2006.01) | |
| *A61B 5/0235* | (2006.01) | |
| *A61B 5/021* | (2006.01) | |
| *A61B 5/1455* | (2006.01) | |

(52) U.S. Cl.
CPC ...... *A61B 5/02233* (2013.01); *A61B 5/02438* (2013.01); *A61B 5/6824* (2013.01); *A61B 5/6843* (2013.01); *B29C 65/1635* (2013.01); *B29C 66/1122* (2013.01); *B29C 70/84* (2013.01); *A61B 5/0235* (2013.01); *A61B 5/02108* (2013.01); *A61B 5/02225* (2013.01); *A61B 5/1455* (2013.01); *A61B 2562/0247* (2013.01); *A61B 2562/12* (2013.01); *A61B 2562/166* (2013.01); *A61B 2562/222* (2013.01); *B29L 2031/3481* (2013.01)

(56) References Cited

U.S. PATENT DOCUMENTS

| | | | | |
|---|---|---|---|---|
| 5,746,213 A | * | 5/1998 | Marks | A61B 5/02233 600/499 |
| 6,443,906 B1 | * | 9/2002 | Ting | A61B 5/022 600/485 |
| 2006/0272134 A1 | * | 12/2006 | Turuani | A44C 5/24 24/71 J |
| 2009/0259101 A1 | * | 10/2009 | Unsai | A61B 1/00096 600/110 |
| 2010/0302914 A1 | * | 12/2010 | Faucher | A44C 5/147 368/282 |
| 2015/0272458 A1 | | 10/2015 | Magniez et al. | |
| 2016/0287104 A1 | * | 10/2016 | Tsunoda | A61B 5/02233 |

FOREIGN PATENT DOCUMENTS

| | | |
|---|---|---|
| JP | H02-010805 A | 1/1990 |
| JP | H06-11701 A | 1/1994 |
| JP | H09-285453 A | 11/1997 |
| JP | 2004-254717 A | 9/2004 |
| JP | 2010-051364 A | 3/2010 |
| JP | 2014-033829 A | 2/2014 |
| WO | 2004-069049 A1 | 8/2004 |

OTHER PUBLICATIONS

International Search Report issued in Application No. PCT/JP2016/089054, dated Mar. 21, 2017 (2 pages).
Written Opinion issued in Application No. PCT/JP2016/089054, dated Mar. 21, 2017 (3 pages).
Decision to Grant a Patent in corresponding Japanese Application No. 2016-251967, dated Jun. 20, 2017 (6 pages).

* cited by examiner

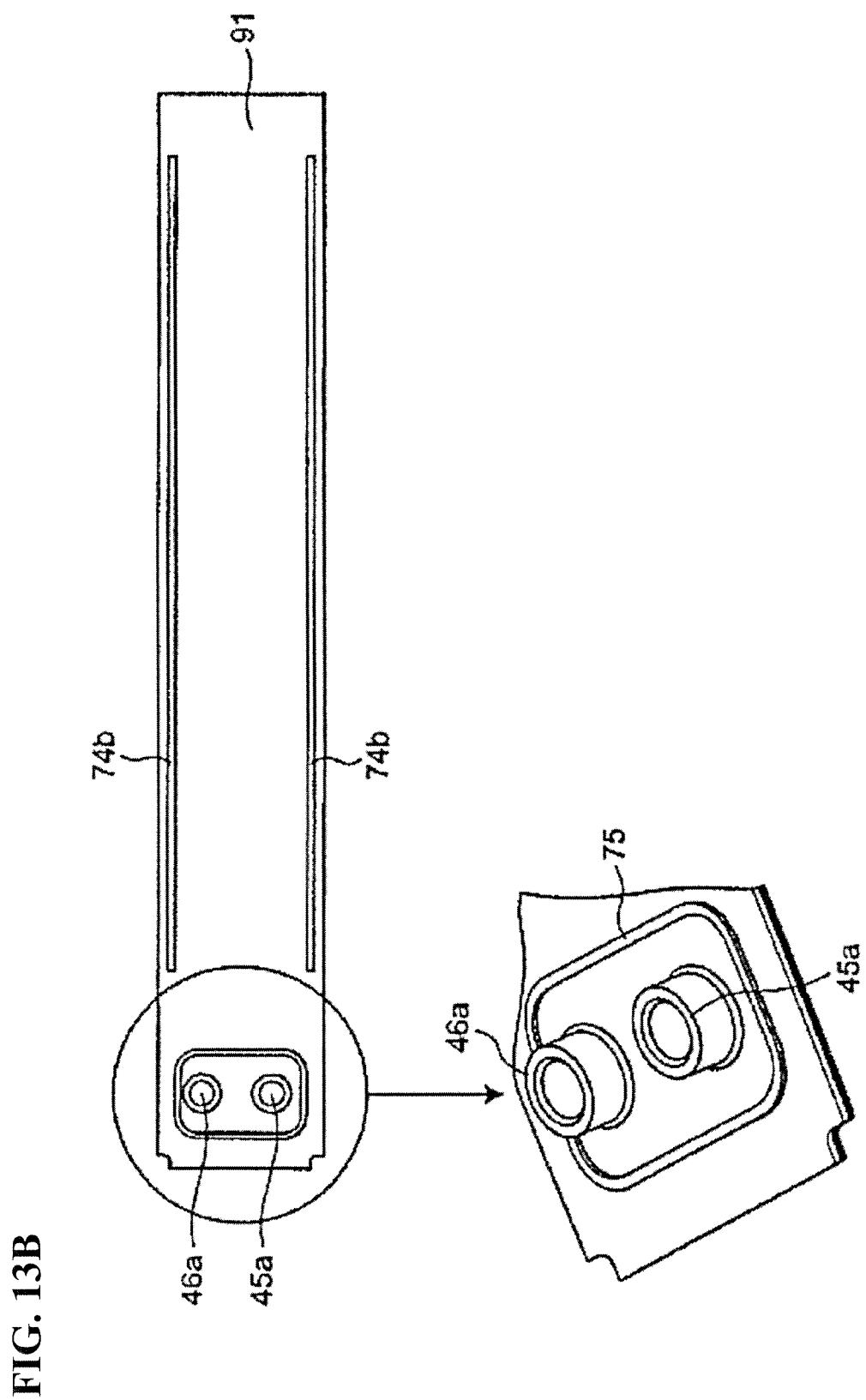

BODILY INFORMATION MEASUREMENT APPARATUS

TECHNICAL FIELD

The present invention relates to a bodily information measurement apparatus, and more specifically relates to a bodily information measurement apparatus that is to be attached to a rod-shaped measurement site such as a wrist, for example.

BACKGROUND ART

In recent years, requirements of wrist-type blood pressure monitors have been increasing. For example, Patent Documents 2 and 3 disclose watch-type blood pressure measurement devices with an arm-wrapping belt (band) to which a cuff (air bladder) is attached, the arm-wrapping belt being attached to both sides of a main body and being fixed to the arm using an adjustment belt. Also, Patent Document 4 discloses a watch-type blood pressure monitor in which the leading end of a belt (band) made of cloth that extends from one end of a blood pressure monitor main body portion is passed through a band ring provided on the end portion on the opposite side of the main body portion, is folded over, and is fixed with Magic Tape (registered trademark). A cuff is constituted such that an air bladder composed of a nylon upper portion and a nylon lower portion is stored inside of the band (cuff case) of the watch-type blood pressure monitor. Here, the cuff is formed so as to be short enough to cover the blood pressure measurement portion and the pump portion so that the cuff is located near the artery, and the main body portion (includes the blood pressure measurement portion and pump portion) is rotated inward of the wrist during blood pressure measurement.

CITATION LIST

Patent Literature

Patent Document 1: JP 2010-51364A
Patent Document 2: JP H6-11701A
Patent Document 3: JP S63-200144A
Patent Document 4: JP H9-285453A

SUMMARY OF INVENTION

However, with the blood pressure measurement device disclosed in Patent Document 2 and Patent Document 3, if the cuff is constituted by a normal watch-type belt that extends to both sides of the main body, the joining portion is located near the radial artery, and therefore the radial artery cannot be correctly compressed, and the blood pressure cannot be accurately measured. Also, with the blood pressure measurement device disclosed in Patent Document 4, since the cuff is not formed so as to go around the wrist, the blood pressure cannot be measured accurately in the state in which the main body portion is located on the backhand side of the wrist. Even if the cuff is extended to the leading end of the band, the cuff will break at the band ring portion or the folded-over portion of the cuff will become thick, whereby the appearance of the wearable device will deteriorate.

In view of this, an advantage of one or more embodiments of the present invention lies in providing a bodily information measurement apparatus that the user can attach with a good appearance to his or her wrist, and that has good measurement accuracy.

In the present specification, "base end portion", "leading end portion", "one end portion", and "other end portion" are not limited to the base end, the leading end, the one end, and the other end respectively, and may denote portions within certain ranges.

Also, "inner surface" denotes a surface on the measurement subject side in a state in which the bodily information measurement apparatus has been attached by being wrapped around the measurement site. "Outer surface" denotes a surface on the side opposite to that of the inner surface in a state in which the bodily information measurement apparatus has been attached by being wrapped around the measurement site.

Also, "bodily information" widely encompasses blood pressure values, a pulse value, an activity amount, a blood oxygen concentration, and the like.

Accordingly, a bodily information measurement apparatus according to one or more embodiments of the present invention is a bodily information measurement apparatus that is to be attached by being wrapped around a rod-shaped measurement site, the bodily information measurement apparatus including:

a band-shaped belt to be wrapped around the measurement site, the belt extending in a lengthwise direction from a base end portion to a leading end portion;

a main body that is connected to the base end portion of the belt, and on which a pressure detection unit and a fluid supply unit are mounted; and a fastening portion that is provided on the main body and is for fastening the belt such that the belt forms a loop shape, wherein the belt is formed by stacking an outer circumferential layer arranged on a side opposite to the measurement site, and a fluid bladder that is arranged on the measurement site side and is for compressing the measurement site by enclosing fluid supplied from the fluid supply unit and swelling, and the fluid bladder extends in the lengthwise direction from the leading end portion to a surface on the measurement site side of the main body and is in communication with the pressure detection unit and the fluid supply unit, in a state in which the surface on the measurement site side of the main body and the leading end portion overlap, the base end portion and the leading end portion are fastened by the fastening portion, and thereby the bodily information measurement apparatus is attached to the measurement site, and bodily information is acquired by the pressure detection unit detecting pressure in the fluid bladder.

With the bodily information measurement apparatus according to one or more embodiments of the present invention, the fluid bladder extends in the lengthwise direction of the belt from the leading end portion to the surface on the measurement site side of the main body. When the base end portion of the belt and the leading end portion of the belt are fastened, the surface on the measurement site side of the main body and the leading end portion of the belt overlap. Accordingly, the fluid bladder overlaps on the backhand side of the wrist. For this reason, the degree of swelling of the fluid bladder on the backhand side of the wrist, or in other words, the swelling of the fluid bladder in the thickness direction, increases, and therefore the pulse can be detected accurately. Also, since outward swelling of the fluid bladder can be suppressed by the outer circumferential layer, it is possible to improve the efficiency of compressing the measurement site. Accordingly, the blood pressure measurement accuracy improves. Furthermore, the appearance improves without the leading end portion of the belt protruding in the fastened state.

With the bodily information measurement apparatus according to an embodiment, the outer circumferential layer and the fluid bladder are formed of an elastomer material.

With the bodily information measurement apparatus of the embodiment, the belt is flexible, and therefore can be wrapped around the wrist, is not likely to get dirty, and can be wiped with a damp cloth.

With the bodily information measurement apparatus according to an embodiment, a first main body-side tube element for supplying a fluid for increasing pressure from the fluid supply unit mounted in the main body into the fluid bladder, and a second main body-side tube element for transferring the pressure in the fluid bladder to the pressure detection unit mounted on the main body using the fluid are provided on a surface of the main body that opposes the fluid bladder, the fluid bladder includes a first bladder-side tube element that fits air-tightly together with the first main body-side tube element in a state of opposing the main body, and a second bladder-side tube element that fits air-tightly together with the second main body-side tube element, and a portion of the fluid bladder that opposes the main body is removably attached to the main body via a reinforcing plate adhered to the portion.

With the bodily information measurement apparatus of this embodiment, the reinforcing plate is bonded to the main body via a screw, and therefore the strength with which the fluid bladder is attached to the main body increases. Furthermore, since the fluid bladder and the reinforcing plate can be easily removed by removing the screw, it is possible to expose the pressure detection portion and the ventilation port of the fluid supply portion. Accordingly, it is possible to perform product testing simply by merely removing the screw.

With the bodily information measurement apparatus according to an embodiment, the reinforcing plate includes a through hole having a shape through which all of the first main body-side tube element, the first bladder-side tube element, the second main body-side tube element, and the second bladder-side tube element pass.

With the bodily information measurement apparatus of the embodiment, the fitting-together during attachment is easier.

With the bodily information measurement apparatus according to an embodiment, a protruding ring that protrudes in the thickness direction is provided on the surface of the fluid bladder that opposes the main body, at a position along an inner side with respect to an edge portion of the through hole of the reinforcing plate.

With the bodily information measurement apparatus of the embodiment, the adhesive between the reinforcing plate and the fluid bladder do not protrude inward with respect to the protruding ring.

With the bodily information measurement apparatus according to an embodiment, an operation unit for inputting an instruction to measure bodily information is arranged at a site other than a specified portion at which the main body is arranged in the lengthwise direction of the belt, and an FPC cable that electrically connects the main body and the operation unit is inserted between the fluid bladder and the outer circumferential layer.

With the bodily information measurement apparatus of the embodiment, the main body and the operation unit are electrically connected by an FPC cable. Accordingly, the belt can be made thinner.

With the bodily information measurement apparatus according to an embodiment, a groove portion for storing the FPC cable is formed in the outer circumferential layer.

With the bodily information measurement apparatus of this embodiment, the belt can be made thinner.

As is evident from the description above, with the bodily information measurement apparatus according to one or more embodiments of the invention, the fluid bladder overlaps on the backhand side of the wrist when the belt leading end is fastened to the main body portion, and therefore the degree of swelling of the fluid bladder on the backhand side of the wrist, or in other words, the swelling of the fluid bladder in the thickness direction, increases, and the bodily information can be detected with good measurement. Furthermore, the appearance improves without the leading end portion of the belt protruding in the fastened state.

BRIEF DESCRIPTION OF DRAWINGS

FIG. 13B is a plan view showing an adhesion surface of a fluid bladder 22 in FIG. 13A.

DESCRIPTION OF EMBODIMENTS

Figure 1A:
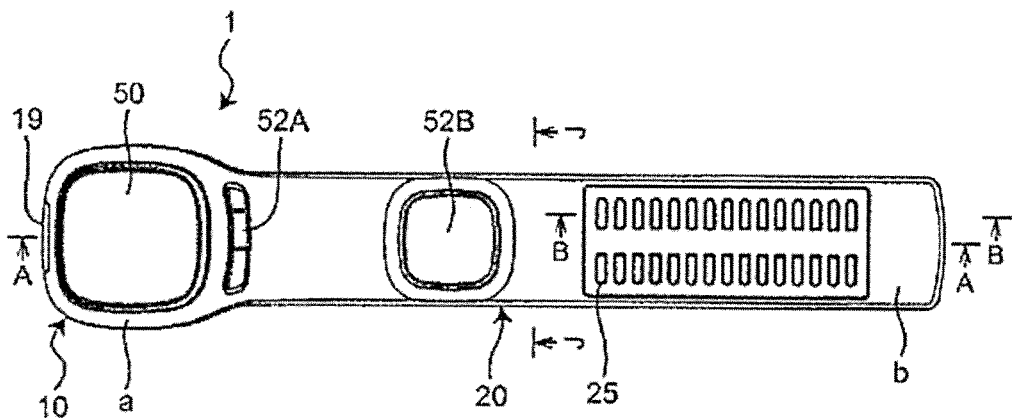
FIG. 1A is a top view showing an exterior of a bodily information measurement apparatus 1 according to a first embodiment of the present invention.

Hereinafter, embodiments according to the present invention will be described with reference to the drawings. Note that in the following embodiments, similar constituent elements are denoted by the same reference numerals and redundant description thereof is not included.

First Embodiment

Figure 1B:
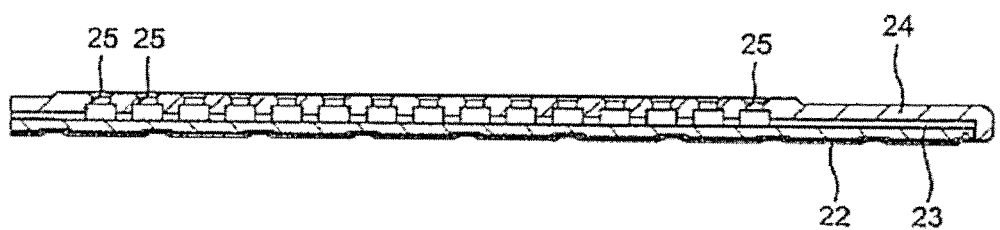
FIG. 1B is a lateral cross-sectional view of the bodily information measurement apparatus 1 taken along line B-B in FIG. 1A.
Figure 1C:
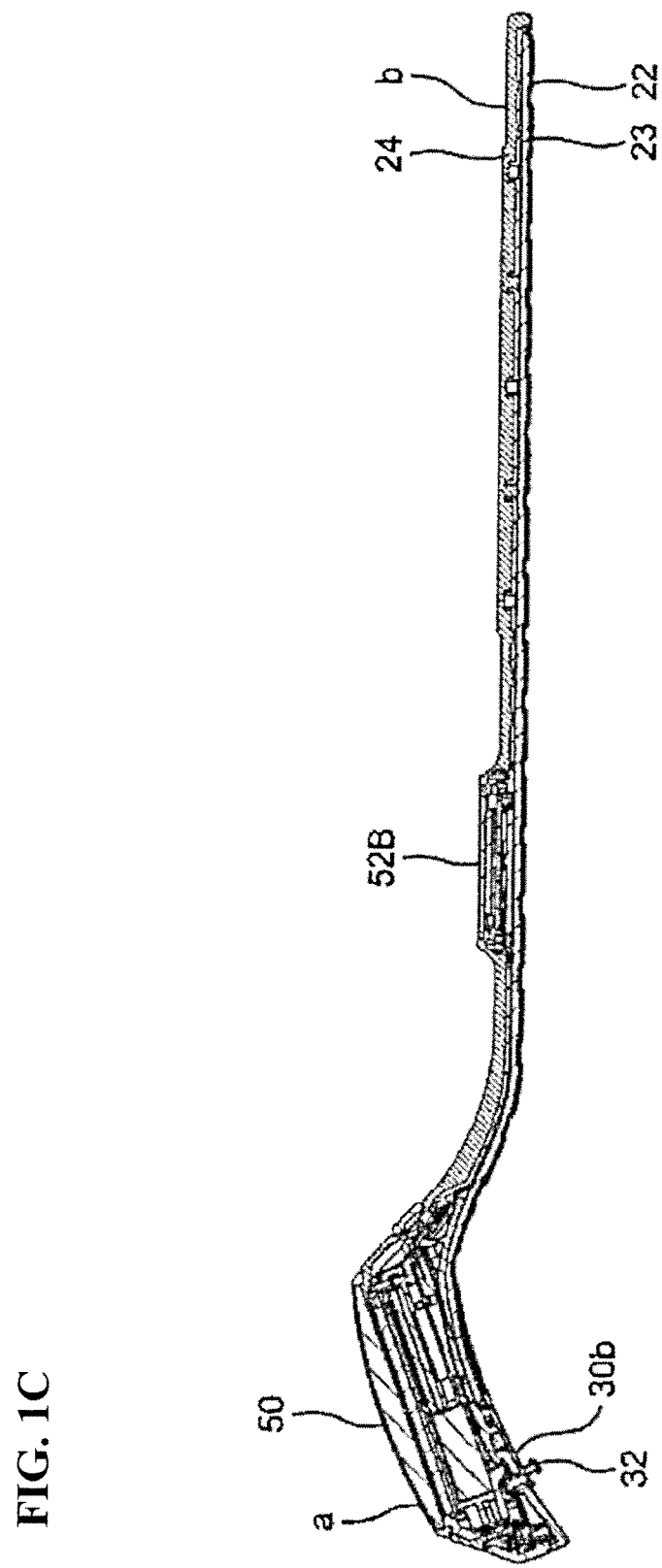
FIG. 1C is a lateral cross-sectional view of the bodily information measurement apparatus 1 taken along line A-A in FIG. 1A.
Figure 2:
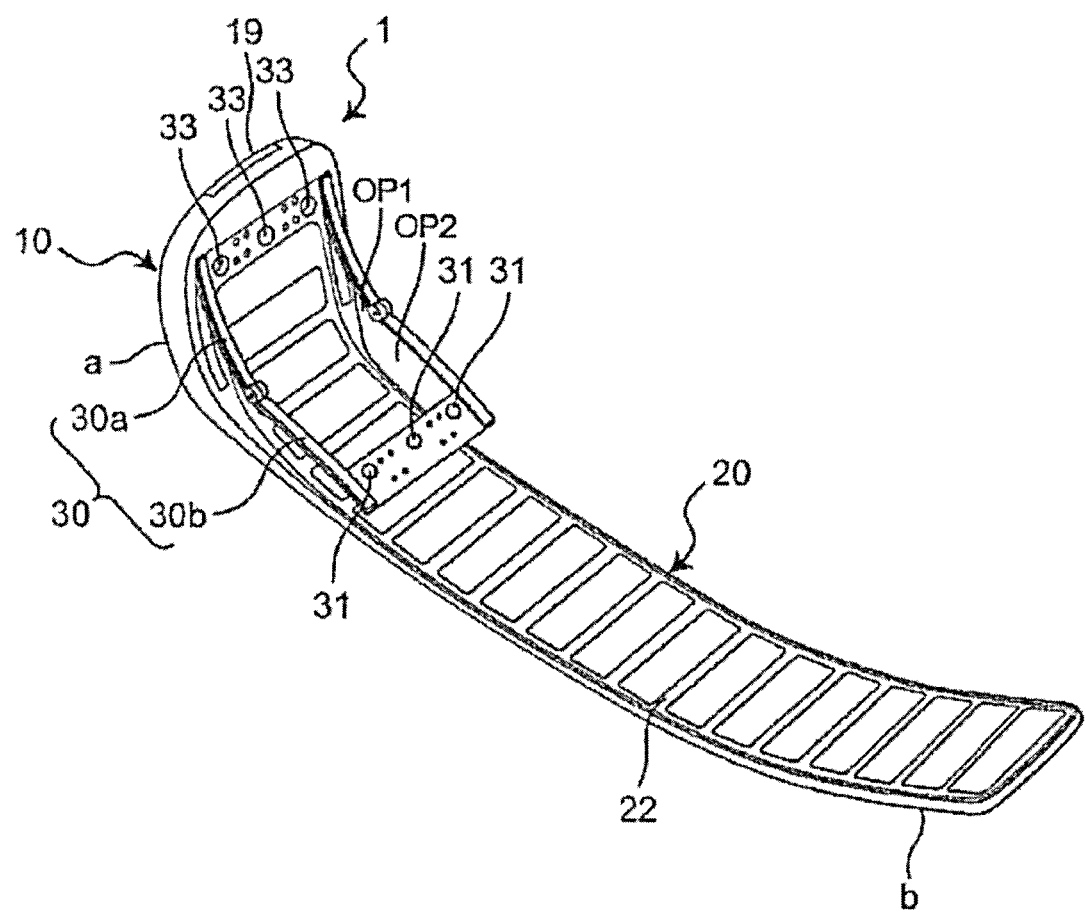
FIG. 2 is a bottom view of the bodily information measurement apparatus 1 shown in FIG. 1.
Figure 4:
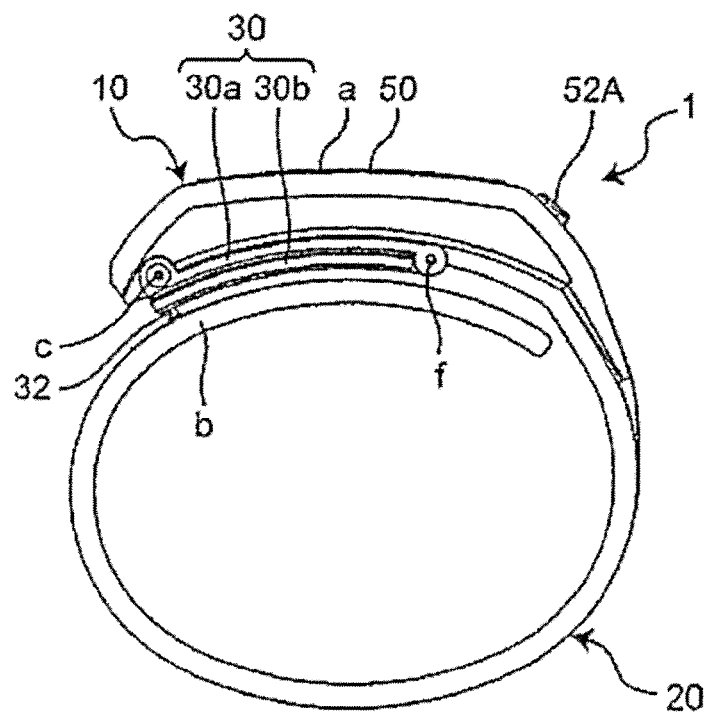
FIG. 4 is a diagram showing a view of the bodily information measurement apparatus 1 in FIG. 3 in a direction orthogonal to the loop of the belt.
Figure 5:
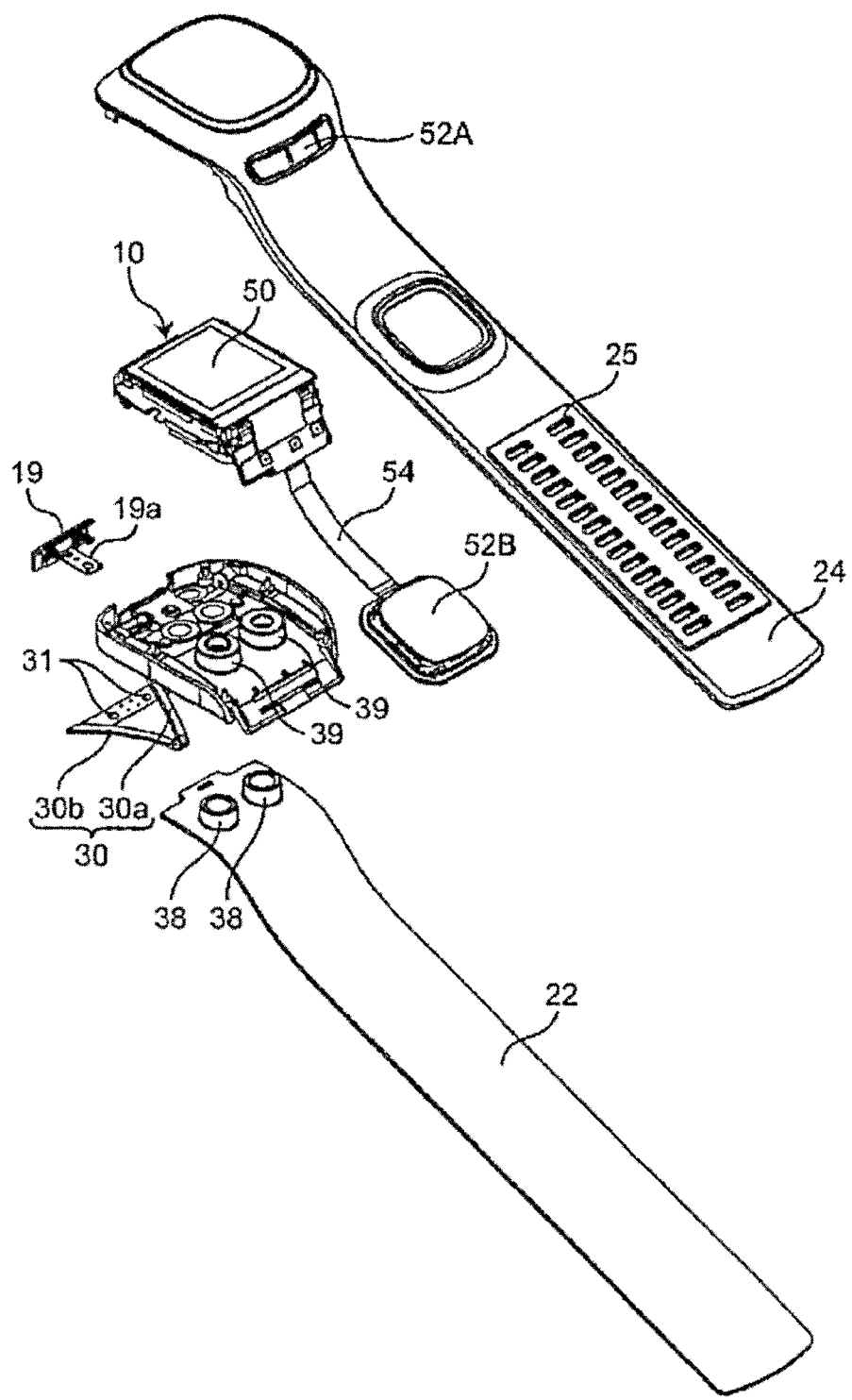
FIG. 5 is an exploded perspective view for illustrating a structure of the bodily information measurement apparatus 1 in FIG. 1A.

FIG. 1A is a top view showing an exterior of a bodily information measurement apparatus 1 according to a first embodiment of the present invention, FIG. 1B is a lateral cross-sectional view of the bodily information measurement apparatus 1 taken along line B-B in FIG. 1A, and FIG. 1C is a lateral cross-sectional view of the bodily information measurement apparatus 1 taken along line A-A in FIG. 1C. Also, FIG. 2 is a bottom view of the bodily information measurement apparatus 1 shown in FIG. 1, FIG. 3 is a perspective view showing a state at a time of attaching the bodily information measurement apparatus shown in FIG. 1 by wrapping it around the measurement site, FIG. 4 is a diagram showing a view of the bodily information measurement apparatus 1 shown in FIG. 3 in a direction orthogonal to the loop of the belt 20, and FIG. 5 is an exploded perspective view for illustrating a structure of the bodily information measurement apparatus 1 shown in FIG. 1A.

Figure 3:
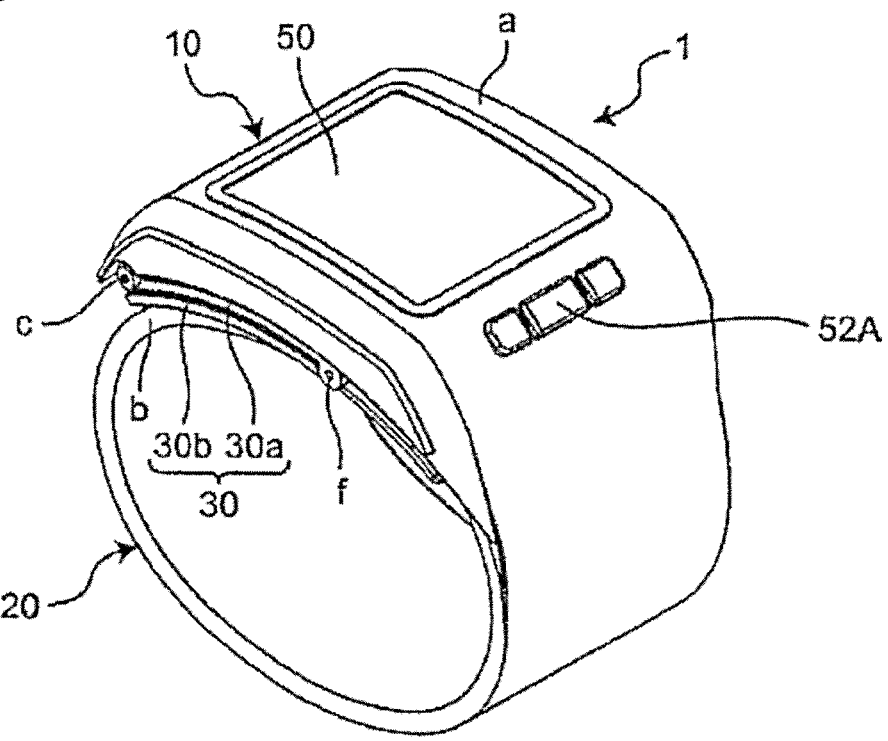
FIG. 3 is a perspective view showing a state at a time when the bodily information measurement apparatus 1 shown in FIG. 1 is formed into a loop shape.

As can be understood from FIG. 3, the bodily information measurement apparatus 1 is attached by being wrapped around a rod-shaped measurement site, such as a wrist 90 (see FIGS. 7A to 7C) of a user, for example, and includes a band-shaped belt 20 that is to be wrapped around the measurement site, a main body 10 that is arranged at a base end portion a in the lengthwise direction of the belt 20 and on which an element for measuring blood pressure is mounted, and a buckle 30 for joining the base end portion a and a leading end portion b on the opposite side in the lengthwise direction of the belt 20 such that the belt 20 becomes a loop shape. Here, the belt 20 serves as a blood pressure measurement cuff. Hereinafter, the structure of the belt 20 will be described.

As can be understood from FIG. 1B, the belt 20 includes a fluid bladder 22 for compressing the measurement site during blood pressure measurement, a reinforcing layer 23 that is provided along the outer surface of the fluid bladder 22 and is for suppressing outward swelling of the fluid bladder 22, and an outer circumferential layer 24 that is provided along the outer surface of the reinforcing layer 23 and covers the reinforcing layer 23. Accordingly, since outward swelling of the fluid bladder 22 can be suppressed, the efficiency of compressing the measurement site can be improved, and the blood pressure measurement accuracy can be further increased. On the other hand, the surface of the fluid bladder 22 (becomes the inner surface when worn) has multiple recesses and protrusions along the lengthwise direction and can easily swell toward the measurement site.

Also, the fluid bladder 22, the reinforcing layer 23, and the outer circumferential layer 24 that are included in the belt 20 are each formed of an elastomer material. For this reason, the belt 20 is flexible, and therefore can be wrapped around the wrist 90, is not likely to get dirty, and can be wiped with a damp cloth.

Furthermore, the hardness of the reinforcing layer 23 is greater than the hardness of the outer circumferential layer 24, which is greater than the hardness of the fluid bladder 22. Accordingly, since the reinforcing layer 23 can suppress outward swelling of the fluid bladder 22 when the fluid bladder 22 swells, the efficiency of compressing the measurement site can be improved. Accordingly, the blood pressure measurement accuracy can be further increased. Furthermore, since the outer circumferential layer 23, which has a hardness that is smaller than the hardness of the reinforcing layer 23, covers the outer circumference of the reinforcing layer 23, the outer circumferential layer 24 of the belt 20 is soft to the touch.

Figure 13A:
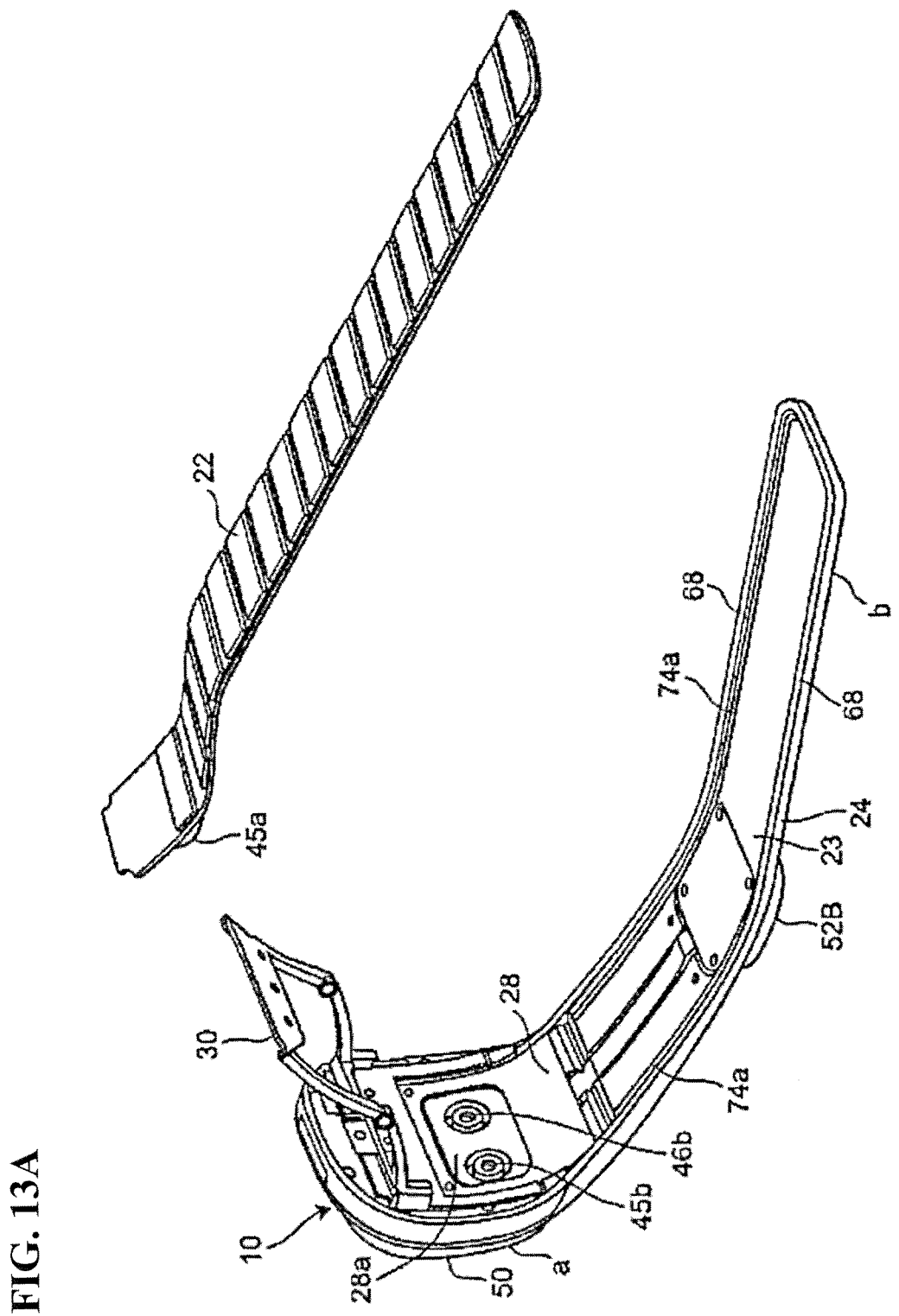
FIG. 13A is an exploded perspective view for illustrating a structure of the belt 20 of the bodily information measurement apparatus 1 in FIG. 1A.
Figure 13C:
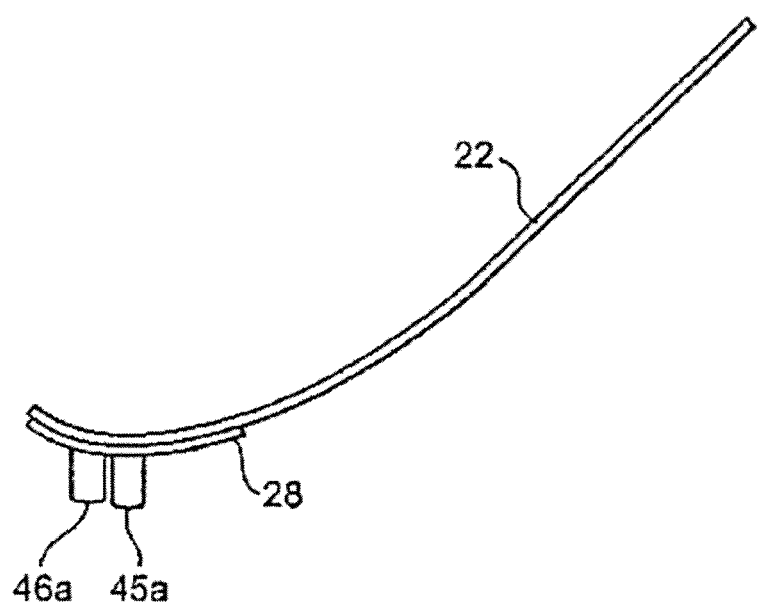
FIG. 13C is a side view schematically showing a state at a time when a reinforcing plate 28 is adhered to the fluid bladder 22 in FIG. 13A.
Figure 13D:
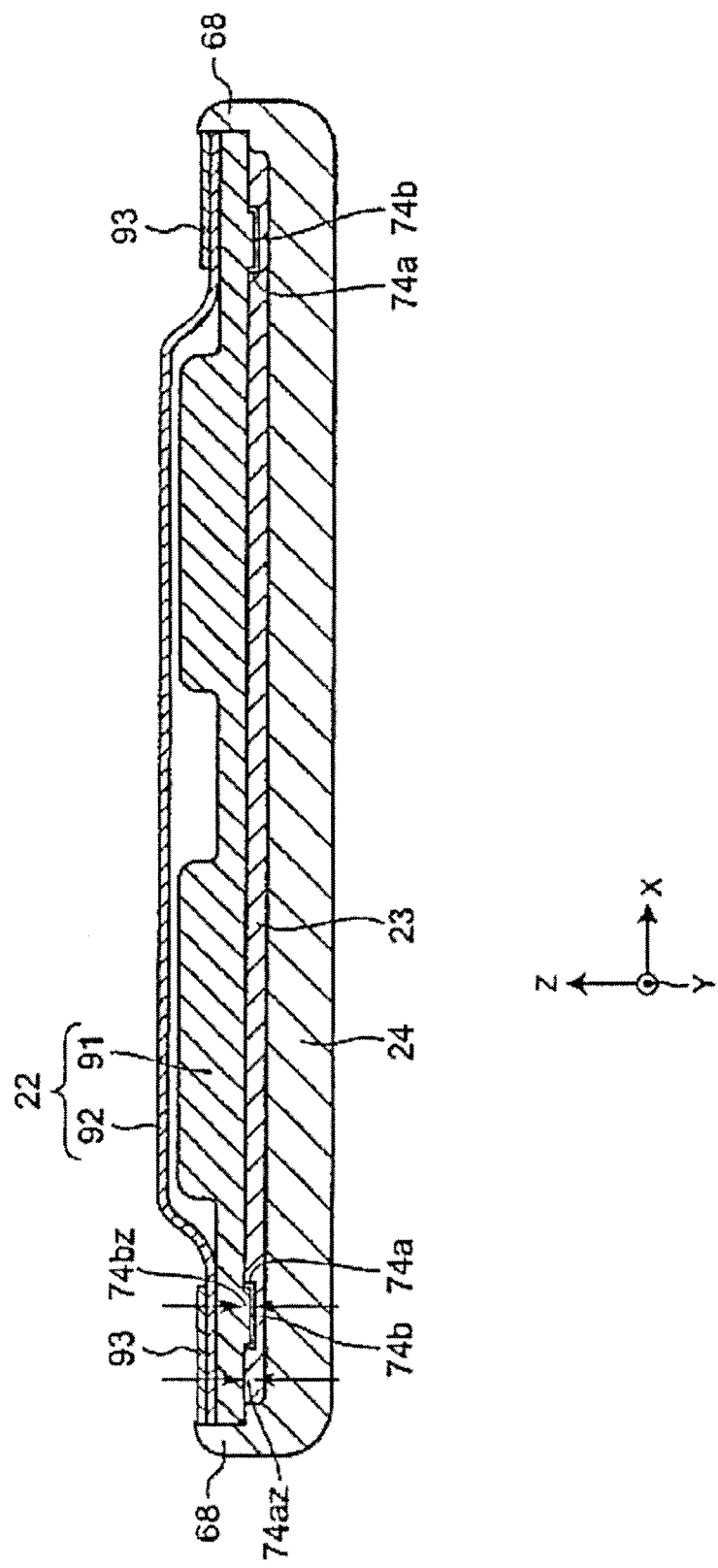
FIG. 13D is a lateral cross-sectional view of the bodily information measurement apparatus 1 taken along line J-J in FIG. 1A.

FIG. 13A is an exploded perspective view for illustrating the structure of the belt 20 of the bodily information measurement apparatus 1 shown in FIG. 1A. Here, a bottom surface of the bodily information measurement apparatus 1 is shown. FIG. 13B is a plan view showing an adhesion surface of the fluid bladder 22 shown in FIG. 13A. FIG. 13C is a side view schematically showing a state at a time when a reinforcing plate 28 is adhered to the fluid bladder 22 shown in FIG. 13A. FIG. 13D is a lateral cross-sectional view of the bodily information measurement apparatus 1 taken along line J-J in FIG. 1A. In FIG. 13D, the width direction of the belt 20 is shown as the X direction, the lengthwise direction is shown as the Y direction, and the thickness direction is shown as the Z direction.

Figure 14A:
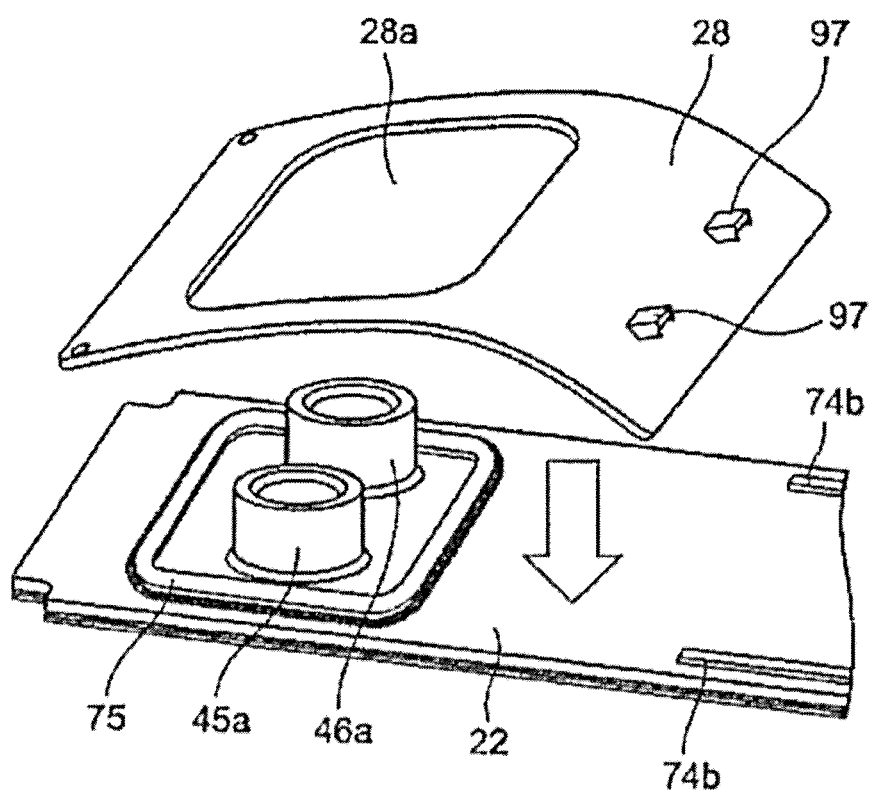
FIG. 14A is a schematic diagram showing a first step of assembling the belt 20 in FIG. 1A.
Figure 14B:
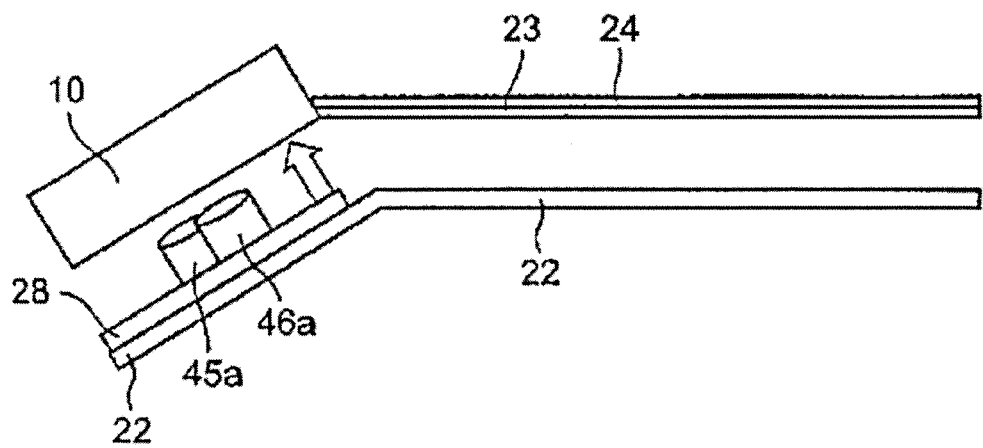
FIG. 14B is a schematic diagram showing a second step of assembling the belt 20 in FIG. 1A.
Figure 14C:
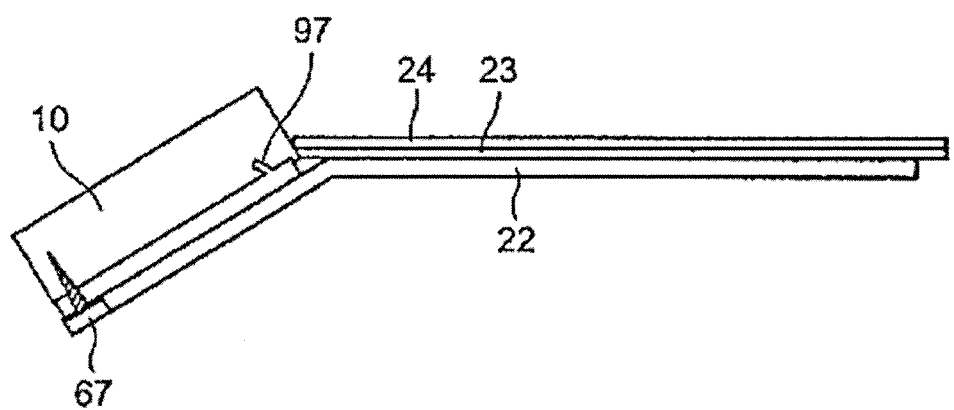
FIG. 14C is a schematic diagram showing a third step of assembling the belt 20 in FIG. 1A.

As shown in FIG. 13A, the main body 10 and the fluid bladder 22 are bonded by fitting the reinforcing plate 28 adhered to the fluid bladder 22 side in the main body 10 and fastening with a screw 67 (see FIG. 14C). The reinforcing plate 28 is adhered to the base end portion a side of the fluid bladder 22 using adhesive. Accordingly, by removing the screw 67, the fluid bladder 22 and the reinforcing plate 28 are removed from the main body 10. However, FIG. 13A shows a state when only the fluid bladder 22 has been removed so that the position of the reinforcing plate 28 at the time when the fluid bladder 22 is bonded to the main body 10 using the screw 67 is clearer.

A ventilation port 45b serving as a first main body-side tube element for supplying a fluid for inflation from a piezoelectric pump 17 (see FIG. 8) mounted in the main body 10 to the interior of the fluid bladder 22, and a ventilation port 46b serving as a second main body-side tube element for transferring the pressure in the fluid bladder 22 to the pressure sensor 16 (see FIG. 8) mounted on the main body 10 using the fluid are provided on a surface of the main body 10 that opposes the fluid bladder 22. The fluid bladder 22 includes a nipple 45a serving as a first bladder-side tube element that fits air-tightly in the ventilation port 45b in a state of opposing the main body 10, and a nipple 46a serving as a second bladder-side tube element that fits air-tightly in the ventilation port 46b. Here, the portion of the fluid bladder 22 that opposes the main body 10 is removably attached to the main body 10 via the reinforcing plate 28 adhered to that portion. With this configuration, the reinforcing plate 28 is bonded to the main body 10 via the screw 67, and therefore the fluid bladder 22 is more strongly attached to the main body 10. Furthermore, by removing the screw 67, the fluid bladder 22 and the reinforcing plate 28 can be easily removed, and therefore the ventilation port of the pressure sensor 16 and the piezoelectric pump 17 can be exposed. Accordingly, it is possible to perform product testing simply using the ventilation ports 45a and 45b by merely removing the screw 67.

Also, a through hole 28a having a shape through which all of the ventilation ports 45b and 46b and the nipples 45a and 46a pass is formed in the reinforcing plate 28. With this configuration, it is easier to fit the nipple 45a and the ventilation port 45b together and to fit the nipple 46a and the ventilation port 46b together.

As shown in FIG. 13B, a protruding ring 75 that protrudes in the thickness direction of the belt 20 is provided at a position along the inner side with respect to the edge portion of the through hole 28a of the reinforcing plate 28 that is to be attached, on the surface of the fluid bladder 22 that opposes the main body 10. With this configuration, the adhesive that is applied between the reinforcing plate 28 and the fluid bladder 22 does not protrude inward with respect to the protruding ring 75.

The portion of the fluid bladder 22 to which the reinforcing plate 28 is not adhered is adhered to the reinforcing layer 23 of the belt 20 with adhesive. As shown in FIGS. 13A and 13D, on the inner circumferential surface of the belt 20, the two edge portions 68 in the width direction (X direction) of the belt 20 protrude in the thickness direction (Z direction) and extend linearly in the lengthwise direction (Y direction). The gap between the two edge portions 68 is narrower than the width of the fluid bladder 22, and the fluid bladder is pressed in the width direction (X direction) of the belt 20 between the two edge portions 68 so as to be adhered to the belt 20. With this configuration, the gap between the two edge portions 68 and the fluid bladder 22 is eliminated in the width direction of the belt 20. For this reason, dust is less likely to accumulate and the appearance improves.

As shown in FIG. 13A, grooves 74a with recessed cross sections extend linearly in the lengthwise direction (Y direction) on the surface of the reinforcing layer 23. The adhesive for adhering the fluid bladder 22 to the reinforcing layer 23 is applied to the grooves 74a. As shown in FIGS. 13B and 13D, protruding lines 74b that fit in the grooves 74a are provided on a base layer 91 of the fluid bladder 22 that opposes the reinforcing layer 23. Due to this configuration, the adhesion step becomes easier, while protrusion of the adhesive is suppressed.

As shown in FIG. 13D, the side surfaces and the bottom surfaces of the protruding lines 74b are adhered to the grooves 74a. Due to this configuration, it is possible to increase the strength of adhesion in the width direction (X direction) and the thickness direction (Z direction) of the belt 20. Note that in the present embodiment, the depth dimension 74a7 of the linear grooves 74a is greater than the height dimension 74bZ of the protruding lines 74b, but one or more embodiments of the present invention are not limited to this. For example, the depth dimension 74a7 of the linear grooves 74a and the height dimension 74bZ of the protruding lines 74b may be made equal. Due to this configuration, it is possible to further increase the strength of adhesion in the width direction (X direction) and the thickness direction (Z direction) of the belt 20.

As shown in FIG. 13D, the fluid bladder 22 includes a base layer 91 that opposes the inner circumferential surface of the belt 20 and a top layer 92 that is arranged so as to overlap with the base layer 91, the edge portions of the base layer 91 and the top layer 92 are welded, and thus a bladder shape is formed. Here, the base layer 91 is less likely to stretch than the top layer 92. Due to this configuration, the base layer 91 is not likely to come off of the inner circumferential surface of the belt 20 when the fluid bladder 22 swells. Note that sheets 93 for preventing lateral bulging of the fluid bladder 22 are further welded in the thickness direction on the edge portions at which the top layer 92 and the base layer 91 are welded. With this configuration, lateral bulging is suppressed when the fluid bladder 22 swells.

Figure 14D:
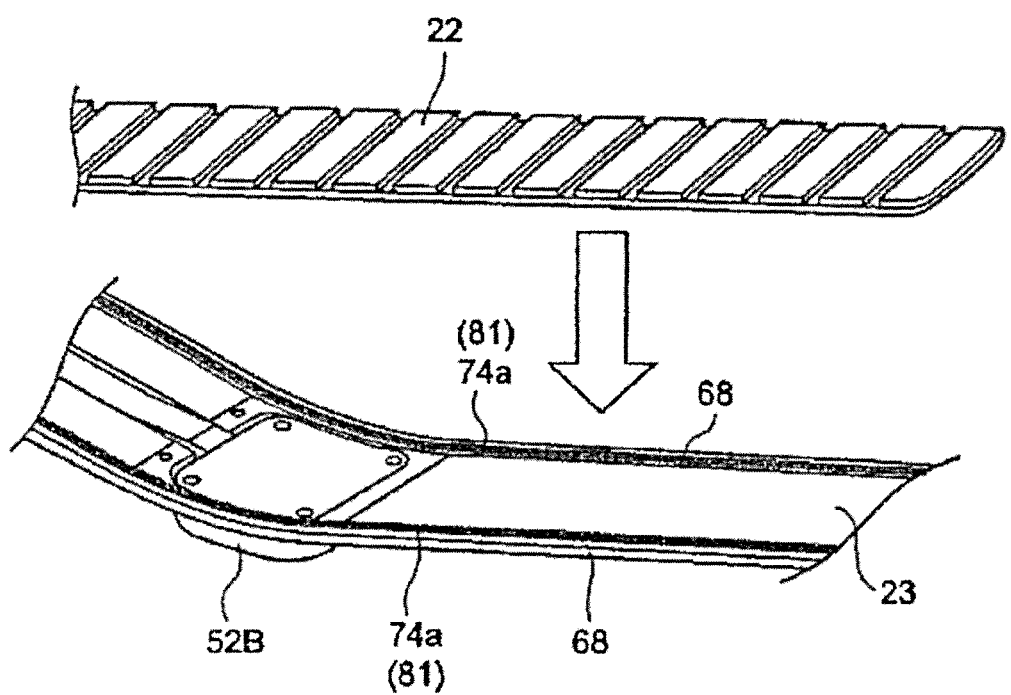
FIG. 14D is a schematic diagram showing a fourth step of assembling the belt 20 in FIG. 1A.
Figure 14E:
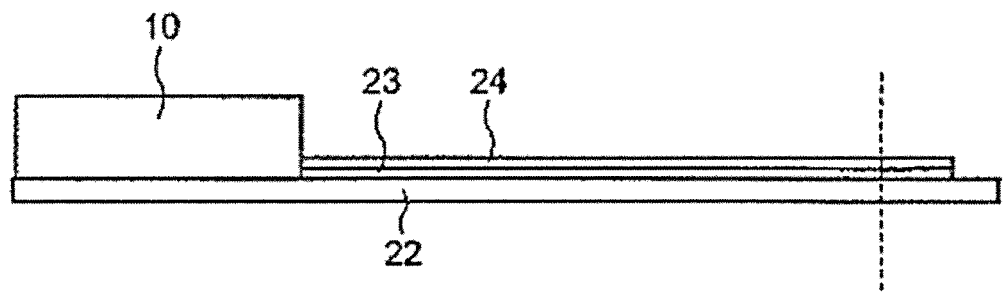
FIG. 14E is a schematic diagram showing a fifth step of assembling the belt 20 in FIG. 1A.
Figure 14F:
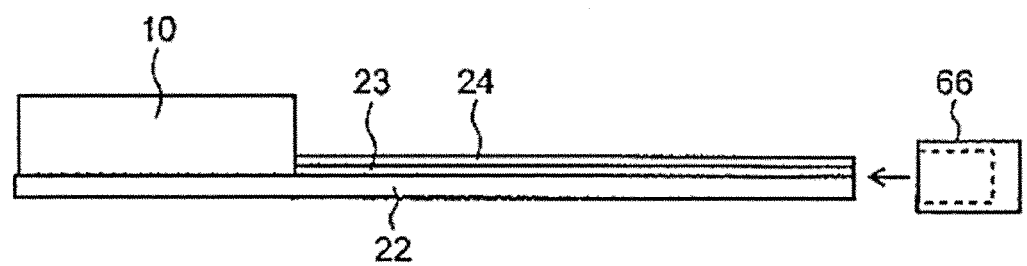
FIG. 14F is a schematic diagram showing a sixth step of assembling the belt 20 in FIG. 1A.

FIGS. 14A to 14F are schematic diagrams showing steps for assembling the belt 20 shown in FIG. 1A. First, as shown in FIG. 14A, the reinforcing plate 28 is adhered to the fluid bladder 22. Next, as shown in FIG. 14B, the nipples 45a and 46a are inserted into the ventilation ports 45b and 46b of the main body 10, and claws 97 of the reinforcing plate 28 are fit into a fit-together portion (not shown) provided on the main body 10 side and fastening is performed with the screw 67 (see FIG. 14C). Next, as shown in FIG. 14D, the reinforcing layer 23 and the fluid bladder 22 are adhered. At this time, the adhesive 81 is allowed to flow into the grooves 74a located several millimeters inward from the two edge portions 68 of the belt 20, and thereafter the fluid bladder 22 is adhered by being bonded. Next, as shown in FIG. 14E, the leading ends of the fluid bladder 22, the reinforcing layer 23, and the outer circumferential layer 24 are cut at the location of the dotted line. Finally, as shown in FIG. 14F, a cap member 66 is bonded to the cut end portion with the adhesive, and the leading ends are collectively covered.

Figure 14G:
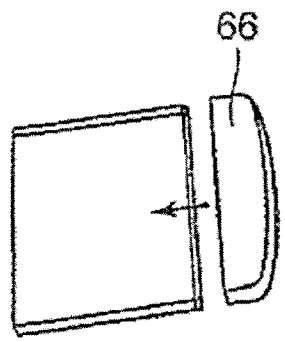
FIG. 14G is a schematic diagram showing a seventh step of assembling the belt 20 in FIG. 1A.

Thereafter, as shown in FIG. 14E, the leading ends of the fluid bladder 22, the reinforcing layer 23, and the outer circumferential layer 24 may be further cut at the location of the dotted line, and then, as shown in FIGS. 14F and 14G, the cap member 66 may be bonded with adhesive at the cut end portions, and the leading end portions may be collectively covered. The cap member 66 is a member that is formed of an elastomer material in which a depression that envelops the leading end portion of the belt 20 is provided. By placing the cap member 66 on the leading end portion of the belt 20, it is possible to conceal positional misalignment that occurs due to dimensional error and the like of the components, between the leading end portion of the reinforcing layer 23 of the belt 20, the leading end portion of the outer circumferential layer 24 of the belt 20, and the leading end portion of the fluid bladder 22 of the belt 20. Accordingly, the appearance of the product improves.

Note that by giving the leading end portion of the belt 20 a rounded shape so as to curve toward the inner circumferential surface and making it easier to slide by forming the cap member 66 with a material having a low friction coefficient, adding a mechanism such as a roller, or the like, it is possible to increase the wearability of the belt 20.

FIG. 15 is a lateral cross-sectional view illustrating a step of a method for manufacturing the fluid bladder 22. The fluid bladder 22 is manufactured using laser transmission welding (LTW). The fluid bladder 22 is formed into a bladder shape overall by overlapping two layers (the base layer 91 and the top layer 92). The sheets 93 for preventing lateral bulging are furthermore overlaid on the edge portions of the fluid bladder 22. Here, one edge portion in the width direction (X direction) has been described. The other edge portion is welded using a similar method as well.

Figure 15A:
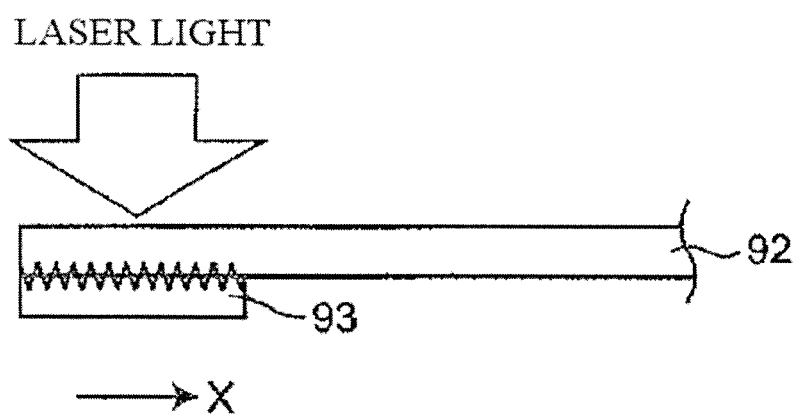
FIG. 15A is a lateral cross-sectional view illustrating a first step of a method for manufacturing the fluid bladder 22 in FIG. 13D.

First, as shown in FIG. 15A, the top layer 92 composed of a light-absorbing material is prepared, and the sheet 93 for preventing lateral bulging, which is composed of a light-absorbing material, is laid on the edge portion on the outer surface of the top layer 92. Next, for example, laser light is emitted from the top layer 92 side over the entire region of the sheet 93 in the width direction (X direction). Upon doing so, the light-absorbing material melts and is welded as overlapping portions, and the sheet 93 is welded. In FIG. 15A (and later-described FIGS. 15B, 16A, and 16B), the welded region is indicated by a triangular wave mark.

Figure 15B:
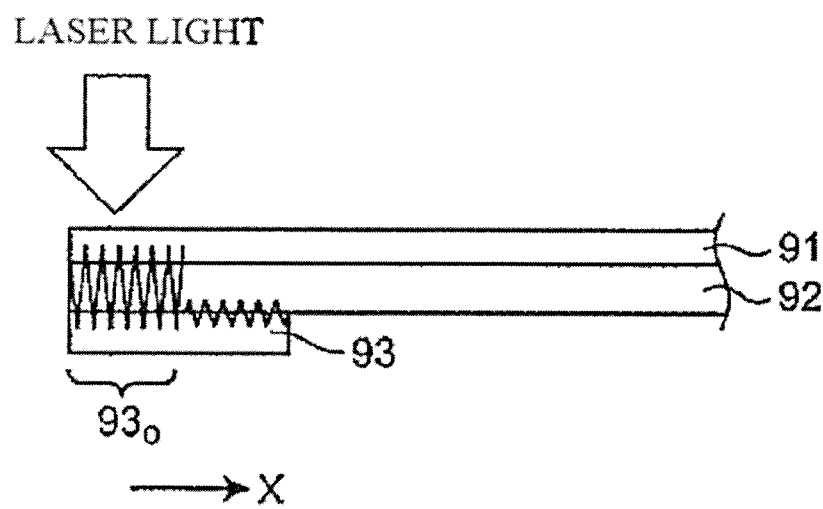
FIG. 15B is a lateral cross-sectional view illustrating a second step of a method for manufacturing the fluid bladder 22 in FIG. 13D.

Next, as shown in FIG. 15B, the base layer 91 composed of a light-transmitting material is laid on the inner surface of the top layer 92. Then, the laser light is once again emitted from the base layer 91 side to only the outside region 93$o$ of the sheet 93 in the width direction (X direction). Upon doing so, the base layer 91 and the top layer 92 are welded at the emission region (outside region 93$o$). Accordingly, the base layer 91 and the top layer 92 are welded and the fluid bladder 22 is formed. Here, the portions of the base layer 91 and the top layer 92 that oppose the sheets 93 for preventing lateral bulging are not welded. With this configuration, it is possible to effectively use the width of the fluid bladder while preventing lateral bulging.

Here, a modified example of a method for manufacturing the fluid bladder 22 will be described. With the method for manufacturing the fluid bladder 22, laser light is emitted twice to the same region (the outside region 93$o$ of the sheet 93). In this case, since laser emission is performed multiple times on the same region, there is a possibility that the material will deteriorate. In contrast to this, in the present modified example, the problem related to deterioration of the material is prevented from occurring by setting the number of emissions of laser light on the same region to one.

FIG. 16 shows lateral cross-sectional views illustrating a modified example of a step of a method for manufacturing the fluid bladder 22 according to a modified example of the first embodiment. Similarly to the example shown in FIG. 15, the fluid bladder 22 is formed into a bladder shape overall by overlapping two layers (the base layer 91 and the top layer 92). The sheet 93 for preventing lateral bulging is furthermore overlaid on the edge portion of the fluid bladder 22. Here, one edge portion in the width direction (X direction) has been described. The other edge portion is welded using a similar method as well.

Figure 16A:
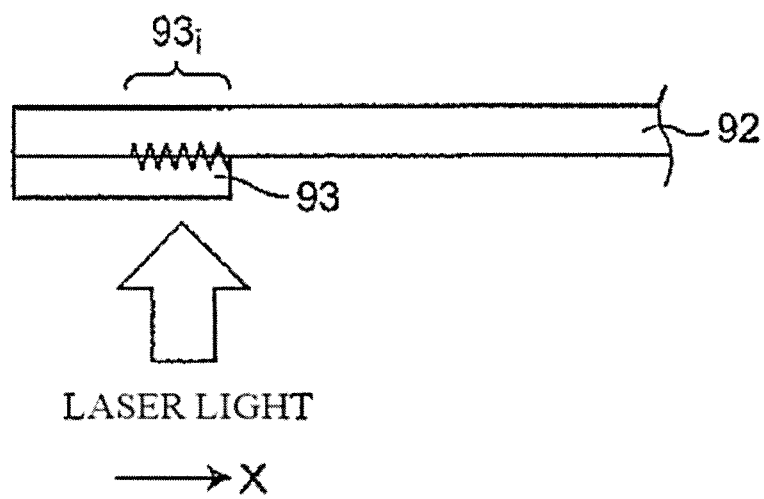
FIG. 16A is a lateral cross-sectional view illustrating a modified example of a first step of a method for manufacturing the fluid bladder 22 in FIG. 13D according to a modified example of the first embodiment.

First, as shown in FIG. 16A, the top layer 92 composed of a light-absorbing material is prepared, and the sheet 93 for preventing lateral bulging, which is composed of a light-absorbing material, is laid on the edge portion on the outer surface of the top layer 92. Next, laser light is emitted from the sheet 93 side to only the inside region 93$i$ of the sheet 93 in the width direction (X direction). Upon doing so, the light absorbing material melts and the sheet 93 is welded at the inside region 93$i$.

Figure 16B:
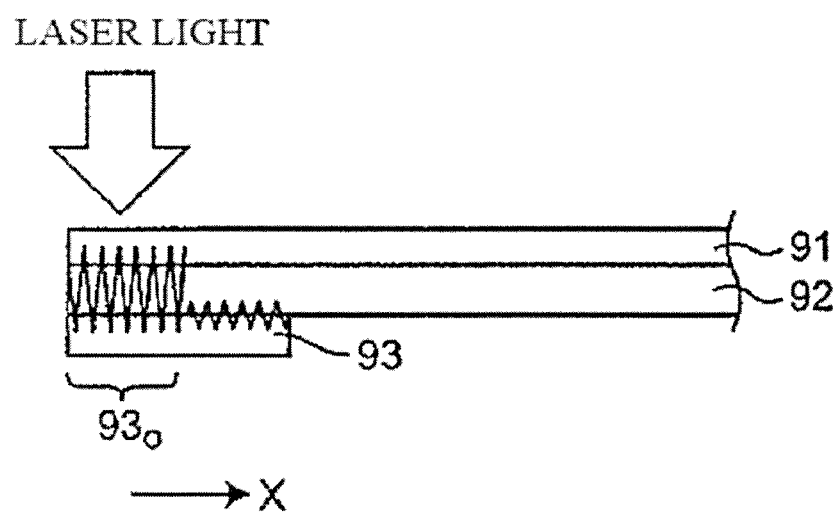
FIG. 16B is a lateral cross-sectional view illustrating a modified example of a second step of a method for manufacturing the fluid bladder 22 in FIG. 13D according to a modified example of the first embodiment.

Next, as shown in FIG. 16B, the base layer 91 composed of a light-transmitting material is laid on the inner surface of the top layer 92. Then, the laser light is once again emitted from the base layer 91 side to only the outside region 93$o$ of the sheet 93 in the width direction (X direction). Upon doing so, the base layer 91 and the top layer 92 are welded at the emission region (outside region 93$o$). Accordingly, the base layer 91 and the top layer 92 are welded and the fluid bladder 22 is formed. Here, laser light can be partially transmitted by making the top layer 92 thinner. Here, the portions of the base layer 91 and the top layer 92 that oppose the sheets 93 for preventing lateral bulging are not welded. With this configuration, it is possible to effectively use the width of the fluid bladder while preventing lateral bulging.

The above-described belt 20 is manufactured as follows.

Figure 10A:
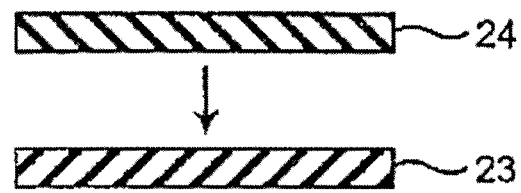
FIGS. 10A to 10C are a lateral cross-sectional view illustrating a step of a method for manufacturing a belt 20 in FIG. 1.
Figure 10B:
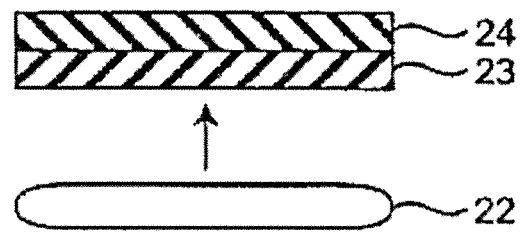
Figure 10C:

FIGS. 10A to 10C are lateral cross-sectional views illustrating steps of a method for manufacturing the belt 20 shown in FIG. 1. As illustrated in FIG. 10A, first, the reinforcing layer 23 is prepared and resin that forms the material of the outer circumferential layer 24 is laid on the outer surface of the reinforcing layer 23 through insert molding. The fluid bladder 22 prepared in advance is adhered or welded as illustrated in FIG. 10B along the inner surface of the reinforcing layer 23 of the intermediate body composed of the reinforcing layer 23 and the outer circumferential layer 24, which were integrated in this manner. In this manner, as illustrated in FIG. 10C, a belt 20 with a three-layer structure, which includes the outer circumferential layer 24, the reinforcing layer 23, and the fluid bladder 22, is formed. Note that in order to facilitate understanding, in the drawings, the resin that forms the material of the outer circumferential layer 24 is denoted by the same reference numeral as the outer circumferential layer 24.

Figure 11A:
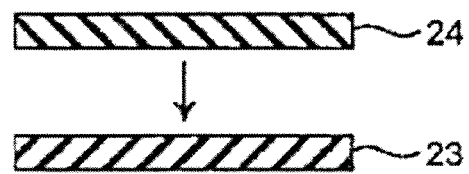
FIGS. 11A to 11C are a lateral cross-sectional view illustrating a step of a method for manufacturing the belt 20 in FIG. 1, according to a modified example of an embodiment of the present invention.
Figure 11B:
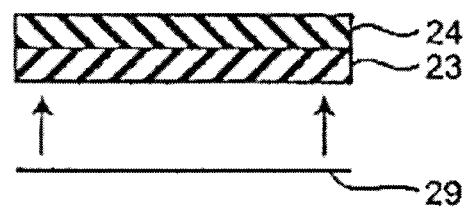
Figure 11C:
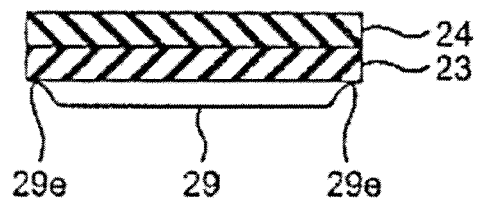

FIGS. 11A to 11C are lateral cross-sectional views illustrating steps of a method for manufacturing the belt 20 in FIG. 1, according to a modified example of an embodiment of the present invention. As illustrated in FIG. 11A, first, the reinforcing layer 23 is prepared and resin that forms the material of the outer circumferential layer 24 is laid on the outer surface of the reinforcing layer 23 through insert molding. Next, as illustrated in FIG. 11B, an intermediate body composed of the reinforcing layer 23 and the outer circumferential layer 24 is manufactured. Also, one sheet 29 is prepared in addition to this. Finally, the fluid bladder 22 composed of the reinforcing layer 23 and the sheet 29 is formed by adhering or welding the circumferential edge portions 29e of the sheet 29 prepared in advance along the inner surface of the reinforcing layer 23 of the intermediate body manufactured as illustrated in FIG. 11C. In this manner, a belt 20 with a three-layer structure including the outer circumferential layer 24, the reinforcing layer 23, and the fluid bladder 22 can be manufactured easily. Note that in order to facilitate understanding, in the drawings, the resin that forms the material of the outer circumferential layer 24 is denoted by the same reference numeral as the outer circumferential layer 24.

Note that the above-described reinforcing layer 23 need not be present, and in such a case, the portion of the reinforcing layer is formed as the outer circumferential layer.

As can be understood from FIGS. 1A, 1B, and 3, an operation portion that includes a blood pressure measurement switch 52B for inputting an instruction to measure bodily information is arranged at a site (in this example, the approximate center portion) that is different from a specific portion (in this example, the base end portion a) at which the main body 10 is arranged in the lengthwise direction of the belt 20. Also, as shown in FIG. 5, an FPC cable 54 that electrically connects the main body 10 and the operation portion 52 is interposed between the fluid bladder 22 and the reinforcing layer 23. Thus, since the main body 10 and the operation portion 52 are electrically connected by the FPC cable 54, the belt 20 can be made thin. Note that in the present embodiment, only the operation unit is arranged, but one or more embodiments of the present invention are not limited to this, and a communication unit and a display unit may be arranged.

As can be understood from FIG. 2, magnets 33 are provided on the inner surface side of the base end portion a of the belt 20, protruding portions 31 made of metal that stick to the magnets 33 are provided on the second plate frame member 30b, and thus a sticking mechanism is formed. With this sticking mechanism, the inner surface side of the base end portion a of the belt 20 or the one end portion d of the first plate frame member 30a and the other end portion h of the second plate frame member 30b can stick to each other. Accordingly, when the main body 10, the first plate frame member 30a, and the second plate frame member 30b of the buckle 30 are folded in on each other, the inner surface of the main body 10, the first plate frame member 30a, and the second plate frame member 30b of the buckle 30 are guided so as to overlap.

Note that in addition to or instead of the above-described sticking mechanism, it is desirable to include a lock mechanism that allows the inner surface side of the base end portion a of the belt 20 or the one end portion d of the first plate frame member 30a and the other end portion h of the second plate frame member 30b to engage with each other. Also, the sticking mechanism and/or the lock mechanism include an unlock mechanism for removing the sticking and/or the engagement according to one or more embodiments of the present invention. In this example, a release button 19 (see FIGS. 1A, 2, and 5) for removing the sticking is provided as an unlocking mechanism on the main body 10. As shown in FIG. 5, a slide board 19a is integrally formed on the release button 19. When the release button 19 is pressed toward the interior of the main body 10, the slide board 19a enters like a wedge between the one end portion d of the first plate frame member 30a and the other end portion h of the second plate frame member 30b shown in FIG. 6B, and the sticking between the first plate frame member 30a and the second plate frame member 30b is removed.

Figure 6A:
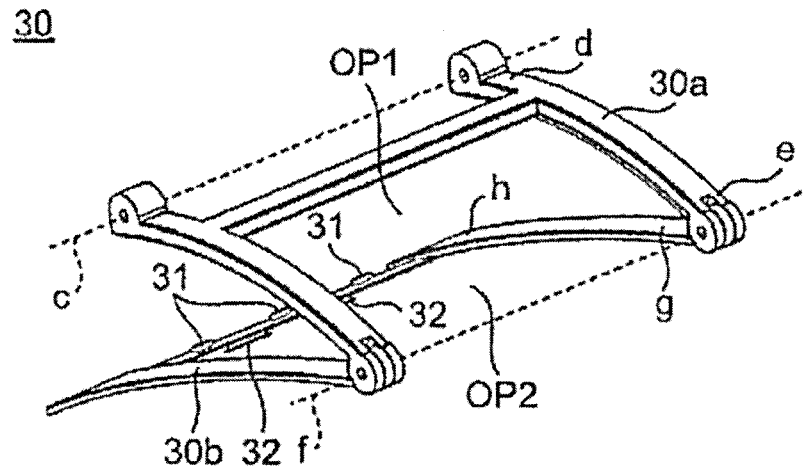
FIG. 6A is a schematic perspective view for illustrating a first state of operations of a buckle 30 in FIG. 5.
Figure 6B:
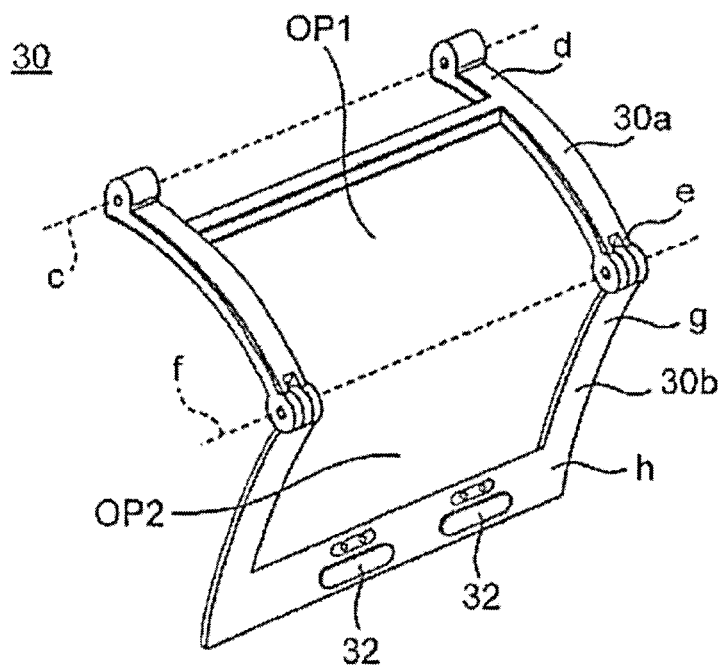
FIG. 6B is a schematic perspective view for illustrating a second state of operations of the buckle 30 in FIG. 5.

As shown in FIGS. 6A and 6B, a first fixing element, which includes engaging portions 32 having protruding shapes, is provided on the inner surface of the other end portion h of the second plate frame member 30b, and as shown in FIGS. 1A, 1B, and 5, a second fixing element, which includes engaged portions 25 having recessed shapes that can engage with the engaging portions 32, is provided on the outer surface of the leading end portion b of the belt 20. Accordingly, as shown in FIGS. 3 and 4, the second plate frame member 30b and the leading end portion b of the belt 20 can be engaged such that the belt 20 is made into a loop shape. Accordingly, the bodily information measurement apparatus 1 can be fixed to the measurement site. Furthermore, since the non-through, recessed second fixing elements (engaged portions 25), which are formed so as to be able to be engaged with the protruding first fixing elements (engaging portions 32), are provided on the outer surface of the leading end portion b of the belt 20, the fixing elements no longer interfere with the fluid bladder 22. Accordingly, the wrist 90 serving as the measurement site can be reliably compressed by the fluid bladder 22 during blood pressure measurement.

Also, as can be understood from FIG. 4, in comparison to Patent Documents 2 to 4, the buckle 30 of the bodily information measurement apparatus 1 according to the present embodiment differs in that it aims to serve as a fastening portion for fastening the base end portion a and the leading end portion b on the opposite side in the lengthwise direction of the belt 20 such that the belt 20 forms a loop shape. In other words, in the state in which the inner surface of the main body 10 and the leading end portion b of the belt 20 overlap, the base end portion a and the leading end portion b are fastened and are attached to the wrist 90 serving as the measurement site by the buckle 30. With this configuration, the inner surface of the main body 10 and the leading end portion b of the belt 20 overlap when the base end portion a of the belt 20 and the leading end portion b of the belt 20 are fastened. Here, as can be understood from FIG. 1C, the fluid bladder 22 extends in the lengthwise direction of the belt 20 from the leading end portion b to the inner surface of the main body 10. Accordingly, the fluid bladder 22 overlaps on the backhand side of the wrist when the base end portion a of the belt 20 and the leading end portion b of the belt 20 are fastened as shown in FIG. 4. For this reason, the degree of swelling of the fluid bladder 22 on the backhand side of the wrist, or in other words, the swelling of the fluid bladder 22 in the thickness direction, increases, and therefore the pulse can be detected accurately. Accordingly, the blood pressure measurement accuracy improves. Furthermore, the appearance improves without the leading end portion b of the belt 20 protruding in the fastened state.

Note that in the present embodiment, a protruding shape was used as the first fixing element and a recessed shape was used as the second fixing element, but one or more embodiments of the present invention are not limited thereto. For example, a recessed shape may be used as the first fixing element and a protruding shape may be used as the second fixing element. In this case as well, an effect similar to that of the present embodiment can be obtained.

As can be understood from FIGS. 1A, 1B, and 5, the engaged portions 25 are formed in alignment in the lengthwise direction of the belt 20 so as to enable adjustment of the attachment position of the other end portion h of the second plate frame member 30b in the lengthwise direction of the belt 20. Accordingly, the attachment position of the other end portion h (see FIG. 6B) of the second plate frame member 30b can be adjusted in the lengthwise direction of the belt 20. Accordingly, the length of the loop of the belt 20 can be set variably so as to exactly match the circumferential length of the wrist 90 serving as the measurement site.

Also, the multiple (in this example, 2) engaged portions 25 are formed in alignment in the width direction of the belt 20. Accordingly, even if the belt 20 twists slightly, the engagement between the engaging portions 32 and the engaged portions 25 is not likely to come off.

Also, at least the outer surface of the leading end portion b of the belt 20 is composed of a flexible material. Accordingly, it is easy to remove the engagement between the engaging portions 32 and the engaged portions 25. Note that it is possible to include a removal mechanism (not shown) according to which the user removes the locking between the engaging portions 32 and the engaged portions 25. In this case, in the state in which the belt 20 is attached to the wrist 90, the user can remove the locking between the engaging portions 32 and the engaged portions 25 using the removal mechanism. Accordingly, removal of the belt 20 is even easier.

FIG. 6A is a schematic perspective view for illustrating a first state of operations of the buckle 30 shown in FIG. 5, and FIG. 6B is a schematic perspective view for illustrating a second state of operations of the buckle 30 shown in FIG. 5.

The buckle 30 includes a first plate frame member 30a that is attached at the one end portion d so as to be able to rotate about the axis c that intersects with the lengthwise direction of the belt 20 on the inner surface side of the base end portion a of the belt 20, and the first plate frame member 30a extends in a curved manner in the form of a plate from the one end portion d to the other end portion e on the opposite side. Also, the second plate frame member 30b attached so as to be able to rotate about an axis f that is parallel to an axis c is included on the other end portion e of the second plate frame member 30a, and the second plate frame member 30b extends in a curved manner in the form of a plate from the one end portion g to the other end portion h on the opposite side.

Furthermore, the other end portion h of the second plate frame member 30b is formed so as to be able to attach to the leading end portion b of the belt 20, and the first plate frame member 30a and the second plate frame member 30b include a first opening portion OP1 and a second opening portion OP2 that penetrate through the plate surfaces of the respective portions. Here, in a state in which the inner surface of the main body 10, the first plate frame member 30a, and the second plate frame member 30b of the buckle 30 are folded over so as to overlap, the first opening portion OP1 of the first plate frame member 30a and the second opening portion OP2 of the second plate frame member 30b are continuous in the thickness direction of the main body 10.

Accordingly, it is possible to use a configuration in which the fluid bladder 22 is arranged so as to compress the measurement site on the inner side of the main body 10.

The first opening portion OP1 opens toward the other end portion e side of the first plate frame member 30a, the second opening portion OP2 opens toward the one end portion g side of the second plate frame member 30b, and the first opening portion OP1 and the second opening portion OP2 are in communication. In other words, the first plate frame member 30a and the second plate frame member 30b are formed into an approximate U shape, and are joined together at the sides at which the opening portions are open. Also, as can be understood from FIG. 2, the fluid bladder 22 for compressing the measurement site during blood pressure measurement is provided along the lengthwise direction of the belt 20 in the belt 20, and the fluid bladder 22 is in communication with the interior of the main body 10 through the region corresponding to the first opening portion OP1 and the second opening portion OP2 in the folded state.

With this configuration, the region of the wrist 90 serving as the measurement site that is spatially continuous from the portion corresponding to the inside of the main body 10 to the leading end portion b of the belt 20 in the circumferential direction can be compressed with the fluid bladder 22. Accordingly, since it is possible to further increase the area with which the air bladder 22 and the measurement site come into contact, the efficiency of compressing the artery can be improved. Accordingly, the blood pressure measurement accuracy can be further increased.

Also, the fluid bladder 22 extends in the lengthwise direction to the leading end portion b of the belt 20. Also, in the state in which the inner surface of the main body 10, the first plate frame member 30a, and the second plate frame member 30b of the buckle 30 are folded so as to overlap, the portion of the main body 10 with which the fluid bladder 22 is in communication overlaps with the portion of the belt 20 at which the fluid bladder 22 is present.

Due to this configuration, the above-described region of the belt 20 that overlaps in the lengthwise direction expands by an amount corresponding to the thickness, which is greater than the thickness of the other regions of the main body 10. Accordingly, the distance by which the artery in the wrist 90 is pushed away by the regions other than the overlapping region decreases, and the extra pressure increase amount for pressing down the artery decreases. As a result, the measurement value of the blood pressure measured by inflating the fluid bladder can be brought closer to the true value, and the measurement accuracy can be increased. Note that the effect of being able to reduce the extra pressure increase amount for pressing down the artery is also achieved in the case where the first opening portion OP1 of the first plate frame member 30a and the second opening portion OP2 of the second plate frame member 30b are omitted in the buckle 30.

Figure 7A:
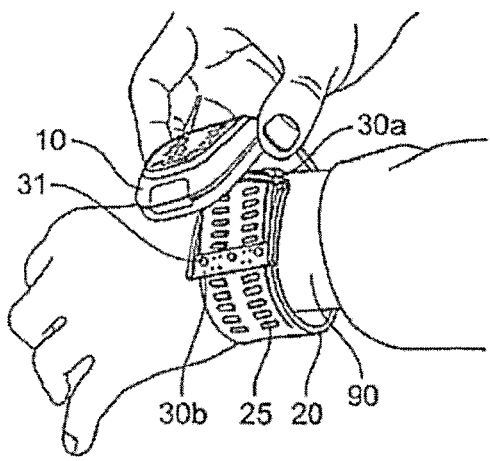
FIG. 7A is a schematic diagram for illustrating a first procedure of performing measurement with the bodily information measurement apparatus 1 in FIG. 1 attached to the wrist.
Figure 7B:
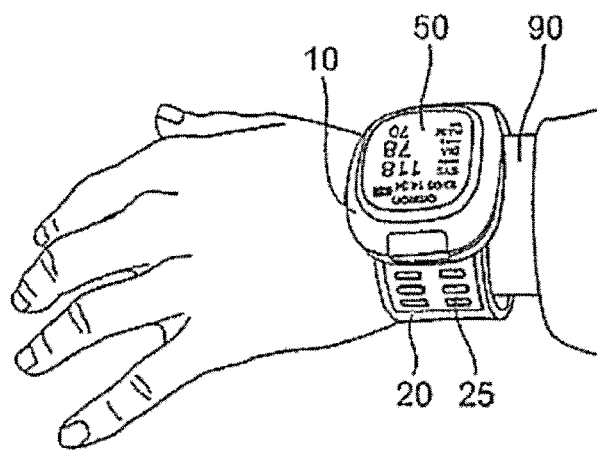
FIG. 7B is a schematic diagram for illustrating a second procedure of performing measurement with the bodily information measurement apparatus 1 in FIG. 1 attached to the wrist.
Figure 7C:
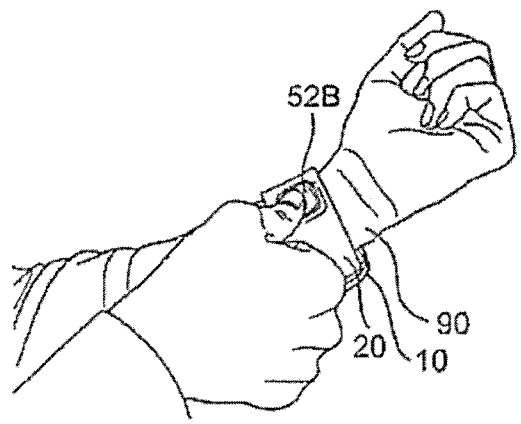
FIG. 7C is a schematic diagram for illustrating a third procedure of performing measurement with the bodily information measurement apparatus 1 in FIG. 1 attached to the wrist.

FIGS. 7A to 7C are schematic diagrams for illustrating a procedure of attaching the bodily information measurement apparatus 1 shown in FIG. 1 to a wrist and performing measurement. When the bodily information measurement apparatus 1 is actually attached to the wrist 90, as shown in FIG. 7A, the user first aligns the belt 20 with the wrist 90 in the state in which the main body 10, the first plate frame member 30a, and the second plate frame member 30b of the buckle 30 are open toward each other. Then, the leading end portion b of the belt 20 is passed through the interior of the second opening portion OP2 (see FIGS. 6A and 6B) of the second plate frame member 30b, and the engaging portions 32 of the second plate frame member 30b are engaged with the engaged portions 25 on the leading end portion b side of the belt 20. Accordingly, the belt 20 is made into a loop, and is set to a state in which the wrist 90 is passed through the loop of the belt 20. Thus, the length of the loop of the belt 20 is set so as to exactly match the circumferential length of the wrist 90.

Next, as shown in FIG. 7B, the main body 10 is brought close to the wrist 90 side, and the inner surface of the main body 10, the first plate frame member 30a, and the second plate frame member 30b of the buckle 30 are folded so as to overlap. Upon doing so, the protrusions 31 of the second plate frame member 30b stick to the magnet 33, whereby the attachment of the bodily information measurement apparatus 1 to the wrist 90 is complete. Next, as shown in FIG. 7C, measurement of the blood pressure is started when the user presses the blood pressure measurement switch 52B.

Figure 8:
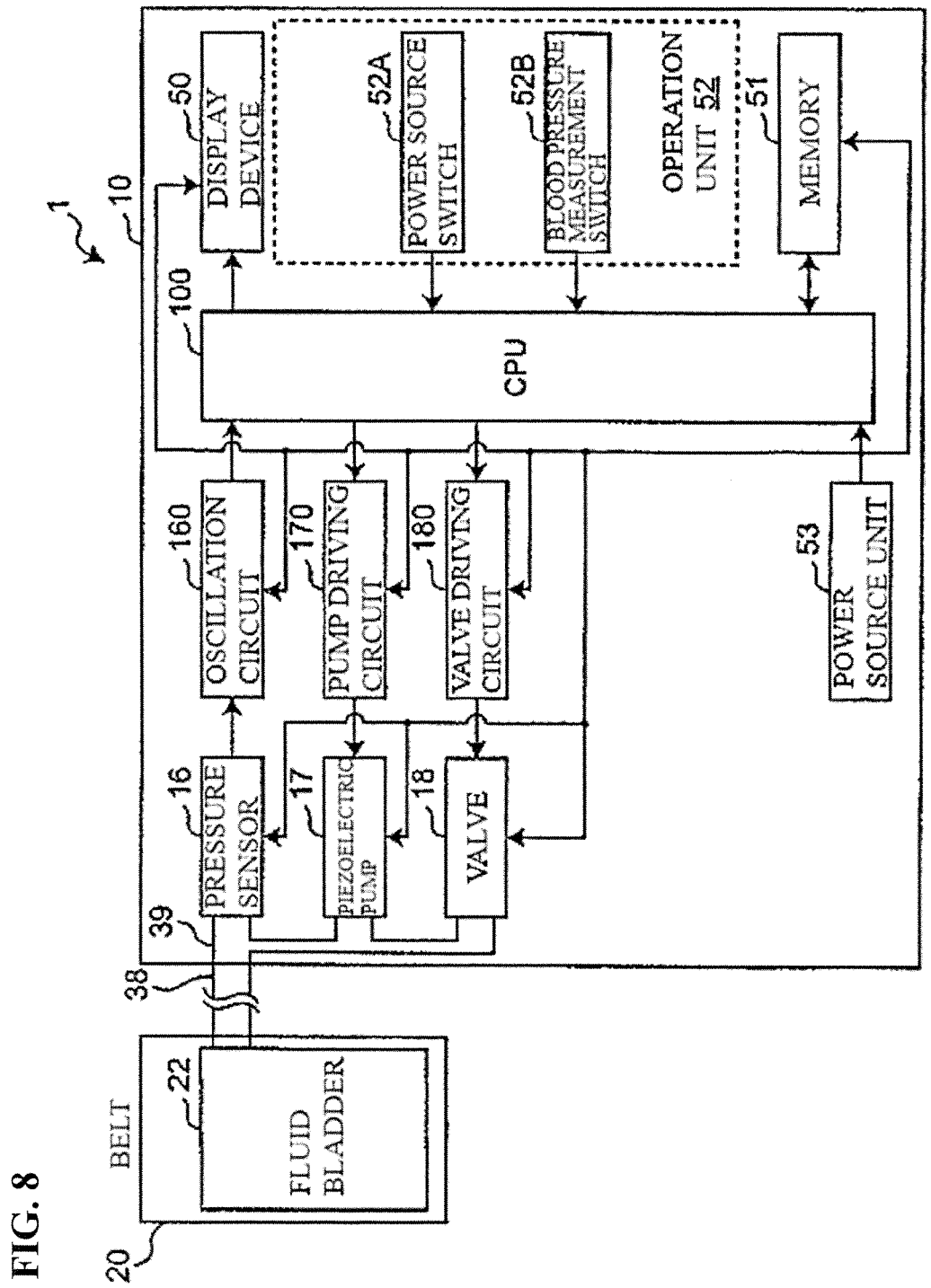
FIG. 8 is a block diagram schematically showing a configuration of control system inside of the bodily information measurement apparatus 1 in FIG. 1.

FIG. 8 is a block diagram schematically showing an internal configuration of the bodily information measurement apparatus 1 shown in FIG. 1. In addition to the above-described display device 50 and the operation unit 52, the main body 10 is provided with a CPU (Central Processing Unit) 100, a memory 51, a power source unit 53, a pressure sensor 16 serving as a piezoresistant pressure detection unit, a piezoelectric pump 17 serving as a fluid supply unit, which is a piezoelectric pump that supplies air serving as a fluid to the fluid bladder 22, a valve 18 for adjusting the pressure (back pressure) on the discharge side of the piezoelectric pump 17, an oscillation circuit 160 that converts the output from the pressure sensor 16 into a frequency, a pump driving circuit 170 that drives the piezoelectric pump 17, and a valve driving circuit 180 that drives the valve 18. The pressure sensor 16, the piezoelectric pump 17, and the valve 18 are connected to the fluid bladder 22 contained in the belt 20 via an air tube 39 provided inside of the main body and a nipple 38 (see FIG. 5) that fits in and is in communication with the air tube 39. Accordingly, the air serving as the fluid flows through the gap between the pressure sensor 16, piezoelectric pump 17, and valve 18, and the fluid bladder 22.

The display device 50 includes a display, an indicator, and the like, and displays predetermined information in accordance with the control signal from the CPU 100.

In the operation unit 52, the power source switch 52A receives an instruction to turn the power source unit 53 on or off. The blood pressure measurement switch 52B receives an instruction to start measuring blood pressure and an instruction to display the data of the measurement results of the blood pressure values stored in the memory 51 on the display device 50. The switches 52A and 52B input operation signals corresponding to instructions given by the user to the CPU 100.

The memory 51 stores programs for controlling the bodily information measurement apparatus 1, setting data for setting various functions of the bodily information measurement apparatus 1, and data of measurement results of blood pressure values. Also, the memory 51 is used as a work memory or the like for when a program is executed.

The power source unit 53 supplies power to the units, namely, the CPU 100, the pressure sensor 16, the piezoelectric pump 17, the valve 18, the display device 50, the memory 51, the oscillation circuit 160, the pump driving circuit 170, and the valve driving circuit 180.

The oscillation circuit 160 oscillates based on an electric signal value based on changes in electrical resistance caused by a piezoresistant effect from the pressure sensor 16 and outputs the frequency signal having a frequency corresponding to the electrical signal value of the pressure sensor 16 to the CPU 100.

The CPU 100 functions as a back pressure control unit in accordance with a program for controlling the bodily information measurement apparatus 1 stored in the memory 51 so as to perform control for driving the piezoelectric pump 17 via the pump driving circuit 170 according to the operation signals from the operation unit 52, and driving the valve 18 via the valve driving circuit 180. The valve 18 opens and closes so as to control the back pressure by discharging or sealing the air in the air bladder 22. Also, the CPU 100 calculates the blood pressure values based on the signal from the pressure sensor 16 and controls the display device 50 and the memory 51.

The piezoelectric pump 17 supplies air as a fluid to the fluid bladder 22 in order to increase the pressure (back pressure) in the fluid bladder 22 contained in the belt 20. The valve 18 opens and closes so as to control the back pressure by discharging or sealing the air in the air bladder 22. The pump driving circuit 170 drives the piezoelectric pump 17 based on the control signal provided by the CPU 100. The valve driving circuit 180 opens and closes the valve 18 based on the control signal provided by the CPU 100.

The pressure sensor 16 and the oscillation circuit 160 operate as a pressure detection unit that detects back pressure. The pressure sensor 16 is, for example, a piezoresistant pressure sensor, and is connected via the air tube 39 to the piezoelectric pump 17, the valve 18, and the fluid bladder 22 contained in the belt 20. In this example, the oscillation circuit 160 oscillates based on an electric signal value based on changes in electrical resistance caused by a piezoresistant effect from the pressure sensor 16 and outputs the frequency signal having the frequency corresponding to the electrical signal value of the pressure sensor 16 to the CPU 100.

Operations of the bodily information measurement apparatus 1 configured as described above will be described below.

Figure 9:
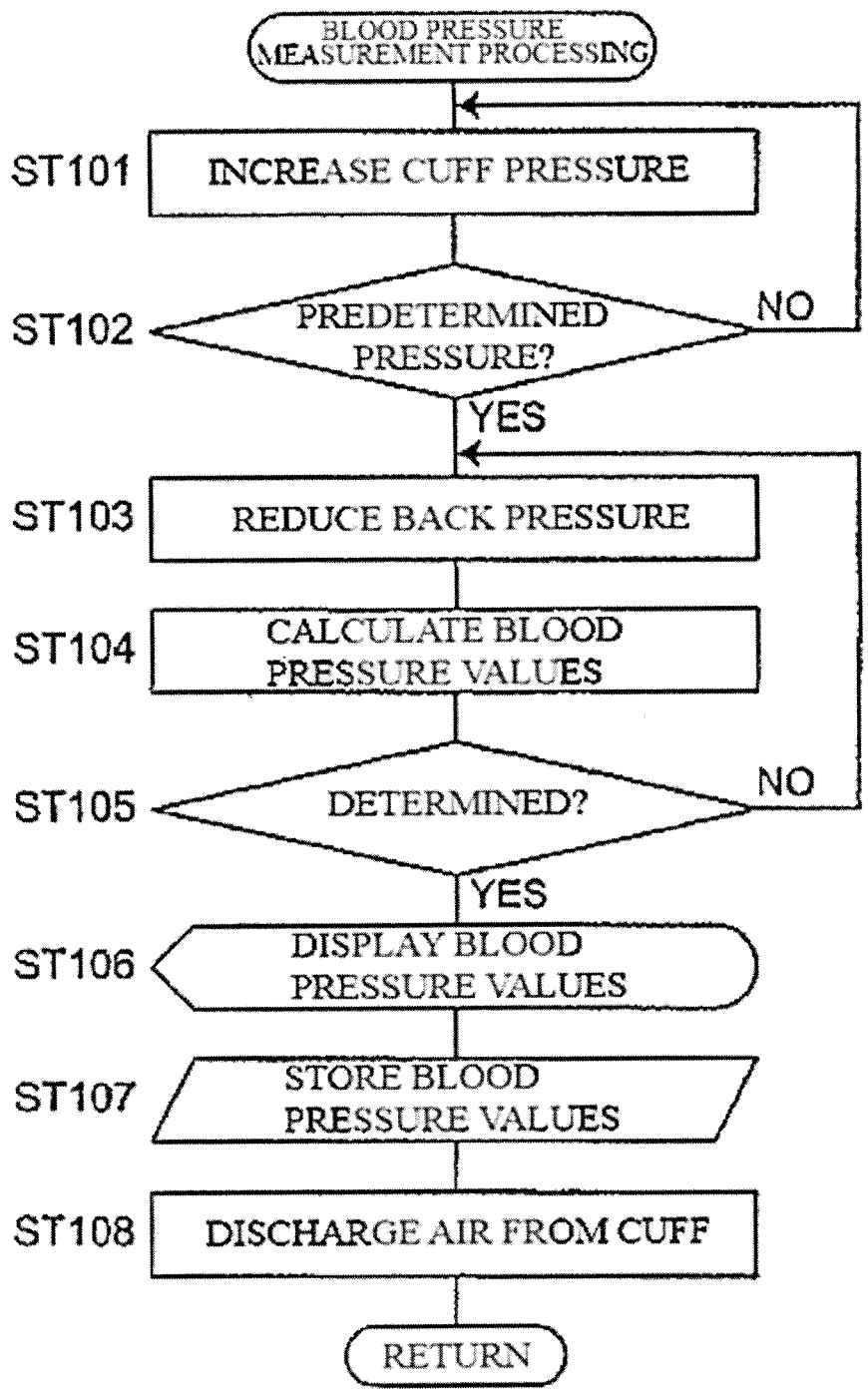
FIG. 9 is a flowchart showing blood pressure measurement processing executed by the bodily information measurement apparatus 1 in FIG. 1.

FIG. 9 is a flowchart showing blood pressure measurement processing executed by the bodily information measurement apparatus 1 shown in FIG. 1. In the case of measuring the blood pressure in accordance with a common oscillometric method, the following operations are generally performed. In other words, the cuff is wrapped around the measurement site (wrist, etc.) of the user in advance, and during measurement, the pump and valve are controlled, the back pressure is increased to be greater than the systolic blood pressure, and thereafter the back pressure is gradually reduced. In the process of reducing the pressure, the back pressure is detected by the pressure sensor, and the variation in the artery volume that occurs in the artery at the measurement site is taken as a pulse wave signal. The systolic blood pressure and the diastolic blood pressure are calculated based on changes in the amplitude of the pulse wave signal accompanying changes in the back pressure at this time (mainly rising edges and falling edges).

With the bodily information measurement apparatus 1, the blood pressure values of the user are measured by the CPU 100 using an oscillometric method according to the flow shown in FIG. 9.

Specifically, when the measurement switch 52B is pressed while the power source switch 52A is on, the bodily information measurement apparatus 1 starts blood pressure measurement as shown in FIG. 9. At the start of blood pressure measurement, the CPU 100 initializes the memory region for processing and outputs a control signal to the valve driving circuit 180. Based on the control signal, the valve driving circuit 180 opens the valve 18 to discharge the air in the fluid bladder 22 of the belt 20. Next, control for adjusting the pressure sensor 16 to 0 mmHg is performed.

In FIG. 9, when the blood pressure measurement is started, first, the CPU 100 closes the valve 18 via the valve driving circuit 180, and thereafter, drives the pump 32 via the pump driving circuit 170 to perform pressure increase processing for sending air to the fluid bladder 22. Accordingly, the fluid bladder 22 is inflated and the back pressure gradually increases (step ST101).

When the cuff pressure is increased and reaches a predetermined cuff pressure (YES in step ST102), the CPU 100 stops the pump 32 via the pump driving circuit 170 and thereafter performs control for gradually opening the valve 18 via the valve control circuit 180. Accordingly, the fluid bladder 22 contracts and the back pressure gradually decreases (step ST103).

Here, the predetermined pressure is a pressure that is sufficiently higher than the systolic blood pressure of the user (e.g., systolic blood pressure+30 mmHg), and is stored in the memory 51 in advance or is determined by the CPU 100 estimating the systolic blood pressure using a predetermined calculation method while the back pressure is increasing (e.g., see JP 2001-70263A).

Also, regarding the pressure decrease speed, a target pressure decrease speed is set while the pressure in the cuff is increased, and the CPU 100 controls the opening degree of the valve 18 so as to reach the target pressure decrease speed (see JP 2001-70263A).

In the process of reducing the pressure, the pressure sensor 16 detects a back pressure signal (indicated by reference sign Pc) that indicates the pressure of the belt 20, via the belt 20. Based on the back pressure signal Pc, the CPU 100 calculates the blood pressure values (systolic blood pressure and diastolic blood pressure) by applying a later-described algorithm through the oscillometric method (step ST104). Note that the calculation of the blood pressure values is not limited to being performed during the pressure reduction process and may be performed during the pressure increase process.

When the blood pressure values are calculated and determined (YES in step ST105), the CPU 100 displays the calculated blood pressure values on the display device 50 (step ST106) and performs control for storing the blood pressure values in the memory 51 (step ST107).

Next, the CPU 100 opens the valve 18 via the valve driving circuit 180 and performs control for discharging the air in the fluid bladder 22 of the belt 20 (step ST108).

Thereafter, when the power source switch 52A is pressed, the blood pressure measurement ends.

In the case of removing the bodily information measurement apparatus 1 from the wrist 90, the user opens the first plate frame member 30a and the second plate frame member 30b of the buckle 30 and removes the wrist 90 from the belt 20 in a state in which the loop of the belt 20 has been made larger.

During the second and subsequent instances of attaching, the wrist 90 need only be passed through the loop of the belt 20 in a state in which the first plate frame member 30a and the second plate frame member 30b of the buckle 30 are open, and the buckle 30 need only be closed. Accordingly, the user can easily attach the bodily information measurement apparatus 1 to the wrist 90.

Second Embodiment

Figure 12A:
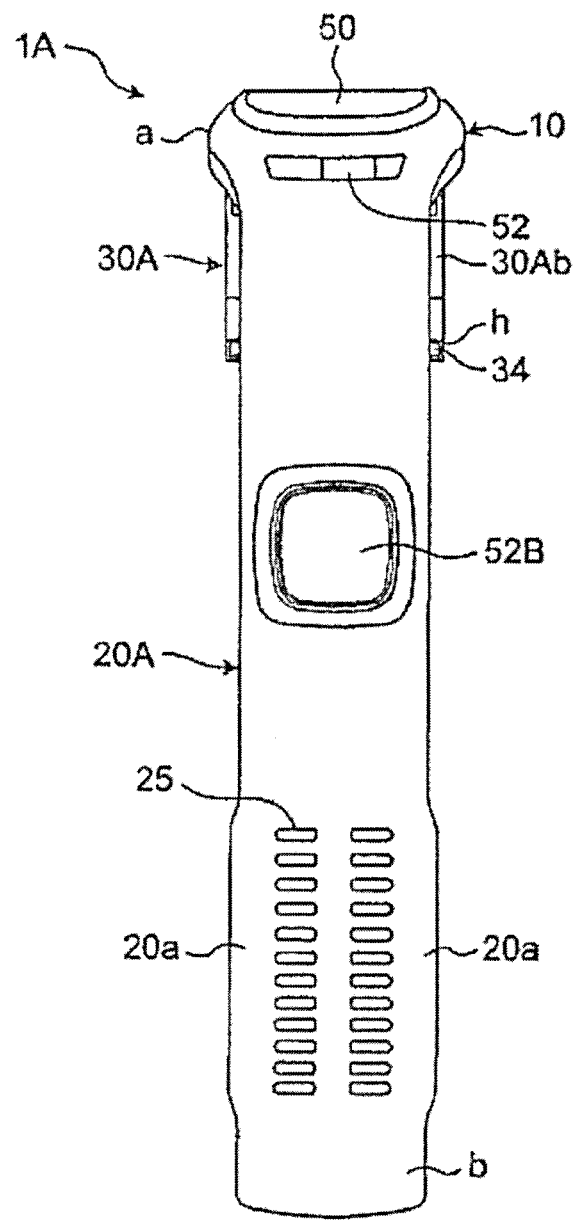
FIG. 12A is a top view showing an exterior of a bodily information measurement apparatus 1A according to a second embodiment of the present invention.
Figure 12B:
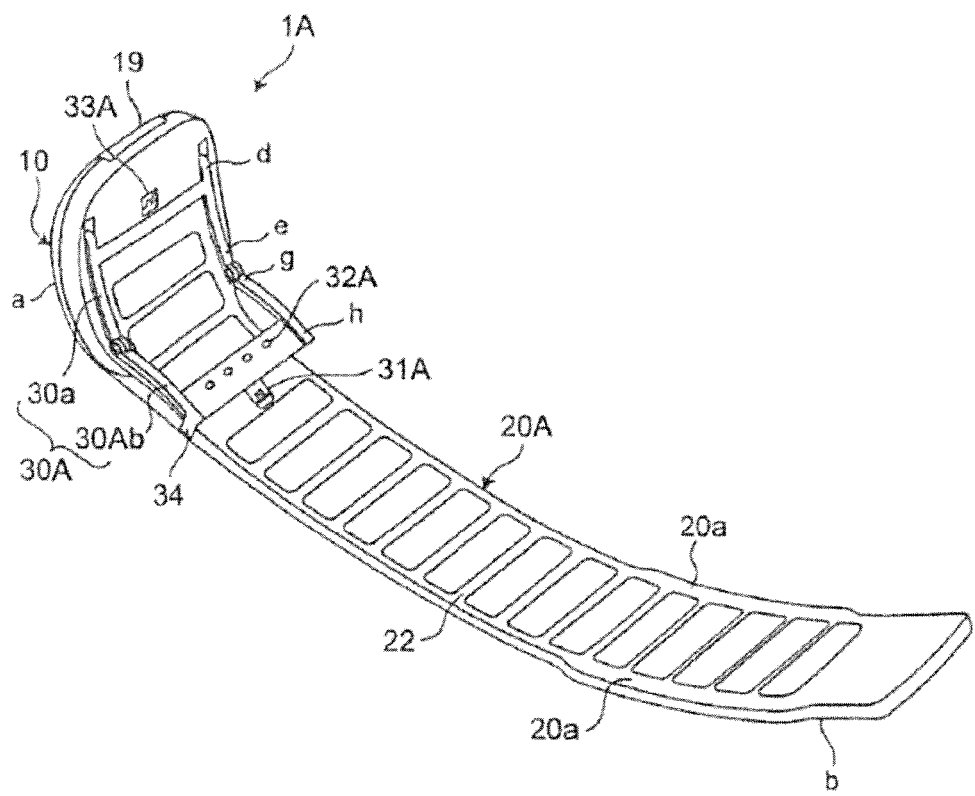
FIG. 12B is a bottom view of the bodily information measurement apparatus 1A in FIG. 12A.

FIG. 12A is a top view showing the exterior of a bodily information measurement apparatus 1A according to a second embodiment of the present invention. FIG. 12B is a bottom view of the bodily information measurement apparatus 1A shown in FIG. 12A, and FIG. 12C is a perspective view showing a state at a time of attaching the bodily information measurement apparatus 1A shown in FIG. 12A by wrapping it around a measurement site.

As shown in FIG. 12A, in comparison to the bodily information measurement apparatus 1 according to the first embodiment, the bodily information measurement apparatus 1A according to the present embodiment differs in that a belt 20A is included instead of the belt 20 and a buckle 30A is included instead of the buckle 30.

Also, as can be understood from FIGS. 12A and 12B, in comparison to the belt 20 according to the first embodiment, the belt 20A according to the present embodiment differs in that wide portions 20a are provided in the width direction, which is perpendicular to the lengthwise direction of the belt 20A. The wide portions 20a are formed on both sides of the second fixing elements (engaged portions 25) in the width direction. In other words, the engaged portions 25 are formed in a wide region of the belt 20A and are formed such that the leading end portion of the belt 20A is wide in the width direction, which is perpendicular to the lengthwise direction of the belt 20A, such that the engaged portions 25 are caught by the leading end portions of later-described hook portions 34.

Figure 12C:
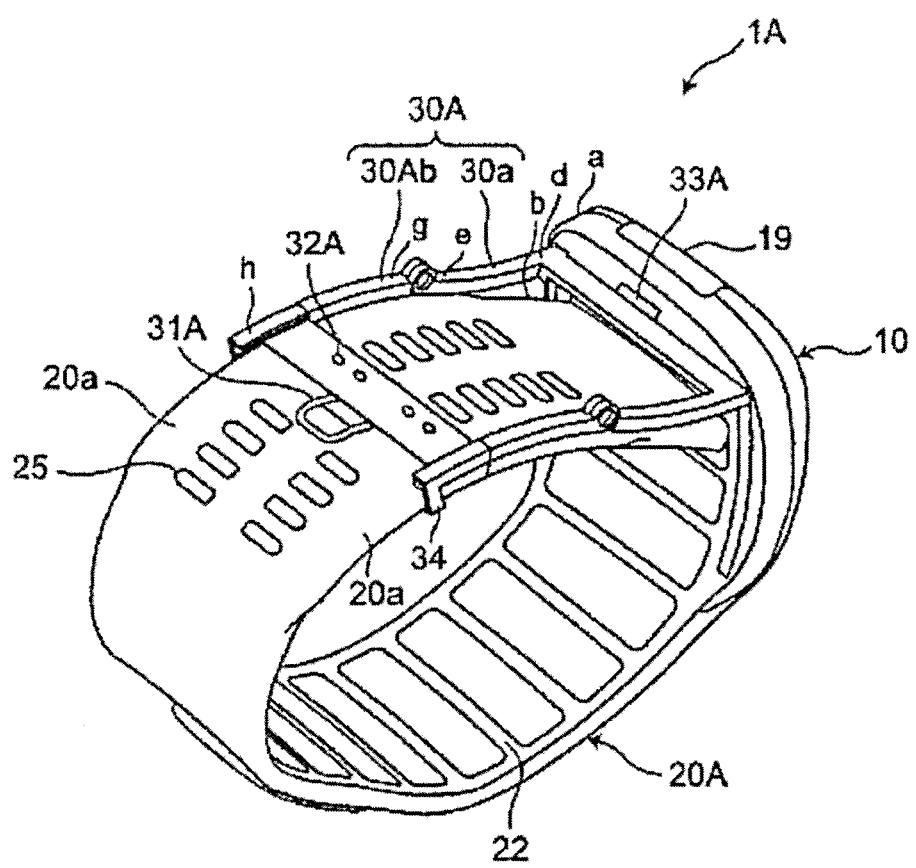
FIG. 12C is a perspective view showing a state at a time of attaching the bodily information measurement apparatus 1 in FIG. 12A by wrapping it around a measurement site.

Also, as can be understood from FIGS. 12B and 12C, in comparison to the buckle 30 according to the first embodiment, the buckle 30A according to the present embodiment differs in that the second plate frame member 30Ab is included instead of the second plate frame member 30b. Here, the first fixing elements including the engaging portions 32A, which has a protruding shape, are provided on the inner surface of the other end portion h of the second plate frame member 30Ab. Along with this, as shown in FIGS. 12A and 12C, second fixing elements including the engaged portions 25, which have recessed shapes that can be engaged with the engaging portions 32A, are provided on the outer surface of the leading end portion b of the belt 20A. Accordingly, as shown in FIG. 12C, the second plate frame member 30Ab and the leading end portion b of the belt 20A can be engaged so as to make the belt 20A into a loop shape. Accordingly, the bodily information measurement apparatus 1A can be fixed to the measurement site. Furthermore, since the non-through, recessed second fixing elements (engaged portions 25), which are formed so as to be able to be engaged with the protruding first fixing elements (engaging portions 32A), are provided on the outer surface of the leading end portion b of the belt 20A, the fixing elements no longer interfere with the fluid bladder 22. Accordingly, the wrist 90 serving as the measurement site can be reliably compressed by the fluid bladder 22 during blood pressure measurement.

As shown in FIGS. 12A, 12B, and 12C, hook-shaped hook portions 34 that are formed so as to protrude are formed on the other end portion h of the second plate frame member 30Ab. The hook portions 34 are locked by catching on the wide portion 20a of the belt 20A. Accordingly, the second plate frame member 30Ab can be reliably fixed to the belt 20A.

As can be understood from FIG. 12B, the engaged portions 33A, which have recessed shapes, are included on the inner surface side of the base end portion a of the belt 20A, and the engaging portions 31A that engage with the engaged portions 33A are included on the second plate frame member 30Ab, and thereby the lock mechanism is configured. With the lock mechanism, it is possible to lock the inner surface side of the base end portion a or the one end portion d of the first plate frame member 30a of the belt 20A together with the other end portion h of the second plate frame member 30Ab. Accordingly, when the main body 10, the first plate frame member 30a, and the second plate frame member 30Ab of the buckle 30A are folded in on each other, the inner surface of the main body 10, the first plate frame member 30a, and the second plate frame member 30Ab of the buckle 30A are fixed so as to overlap.

As can be understood from FIGS. 12A and 12C, multiple engaged portions 25 are formed in alignment in the lengthwise direction of the belt 20A so as to enable the attachment position of the other end portion h of the second plate frame member 30Ab to be adjusted in the lengthwise direction of the belt 20A. Accordingly, the attachment position of the other end portion h (see FIG. 12C) of the second plate frame member 30Ab can be adjusted in the lengthwise direction of the belt 20A. Accordingly, the length of the loop of the belt 20A is variable and thus can be set so as to exactly match the circumferential length of the wrist 90 serving as the measurement site.

In the above-described embodiment, a wrist was used as the measurement site, but the present embodiment is not limited to this. For example, the measurement site may be an arm or a leg. Also, the bodily information measurement apparatuses 1 to 11 according to one or more embodiments of the present invention need not merely measure blood pressure values, and may also measure other bodily information, such as a pulse count.

The above-described embodiments are merely exemplary, and various modifications are possible without departing from the scope of the invention. The above-described multiple embodiments can be achieved independently, but the embodiments can also be combined. Also, the various characteristics in the different embodiments can be achieved independently, and the characteristics in the different embodiments can also be combined.

REFERENCE SIGNS LIST 1, 1A Bodily information measurement apparatus
10 Main body
16 Pressure sensor
17 Piezoelectric pump
18 Valve
20, 20A Belt
22 Fluid bladder
23 Reinforcing layer
24 Outer circumferential layer
25 Engaged portion
29 Sheet
30, 30A Buckle
30a First plate frame member
30b, 30Ab Second plate frame member
31 Protruding portion
31A, 32, 32A Engaging portion
33 Magnet
34 Hook portion
38 Nipple
39 Air tube
50 Display device
51 Memory
52 Operation portion
52A Power source switch
52B Blood pressure measurement switch
53 Power source unit
66 Cap member
160 Oscillation circuit
170 Pump driving circuit
180 Valve driving circuit
100 CPU

The invention claimed is:

1. A bodily information measurement apparatus that is to be attached by being wrapped around a rod-shaped measurement site, the bodily information measurement apparatus comprising:
   a band-shaped belt to be wrapped around the measurement site, the belt extending in a lengthwise direction from a base end portion to a leading end portion;
   a main body that is connected to the base end portion of the belt, and on which a pressure detection unit and a fluid supply unit are mounted; and
   a fastening portion that is provided on the main body and is for fastening the belt such that the belt forms a loop shape,
   wherein the belt is formed by stacking an outer circumferential layer arranged on a side opposite to the measurement site, and a fluid bladder that is arranged on the measurement site side and is for compressing the measurement site by enclosing fluid supplied from the fluid supply unit and swelling, and the fluid bladder extends in the lengthwise direction from the leading end portion to a surface on the measurement site side of the main body and is in communication with the pressure detection unit and the fluid supply unit,
   wherein in a state in which the surface on the measurement site side of the main body and the leading end portion overlap, the base end portion and the leading end portion are fastened by the fastening portion, and thereby the bodily information measurement apparatus is attached to the measurement site,
   wherein bodily information is acquired by the pressure detection unit detecting pressure in the fluid bladder,
   wherein a first main body-side tube element for supplying a fluid for increasing pressure from the fluid supply unit mounted in the main body into the fluid bladder, and a second main body-side tube element for transferring the pressure in the fluid bladder to the pressure detection unit mounted on the main body using the fluid are provided on a surface of the main body that opposes the fluid bladder,
   wherein the fluid bladder includes a first bladder-side tube element that fits air-tightly together with the first main body-side tube element in a state of opposing the main body, and a second bladder-side tube element that fits air-tightly together with the second main body-side tube element, and
   wherein a portion of the fluid bladder that opposes the main body is removably attached to the main body via a reinforcing plate adhered to the portion.

2. The bodily information measurement apparatus according to claim 1, wherein the outer circumferential layer and the fluid bladder are formed of an elastomer material.

3. The bodily information measurement apparatus according to claim 1, wherein the reinforcing plate includes a through hole having a shape through which all of the first main body-side tube element, the first bladder-side tube element, the second main body-side tube element, and the second bladder-side tube element pass.

4. The bodily information measurement apparatus according to claim 3, wherein a protruding ring that protrudes in a thickness direction is provided on the surface of the fluid bladder that opposes the main body, at a position along an inner side with respect to an edge portion of the through hole of the reinforcing plate.

5. The bodily information measurement apparatus according to claim 1,
   wherein an operation unit for inputting an instruction to measure bodily information is arranged at a site other than a specified portion at which the main body is arranged in the lengthwise direction of the belt, and
   wherein an FPC cable that electrically connects the main body and the operation unit is inserted between the fluid bladder and the outer circumferential layer.

6. The bodily information measurement apparatus according to claim 5, wherein a groove portion for storing the FPC cable is formed in the outer circumferential layer.

* * * * *